US006677330B1

(12) United States Patent
Iimura et al.

(10) Patent No.: US 6,677,330 B1
(45) Date of Patent: Jan. 13, 2004

(54) FLUORIDES OF 4-SUBSTITUTED PIPERIDINE DERIVATIVES

(75) Inventors: Yoichi Iimura, Ibaraki (JP); Takashi Kosasa, Ibaraki (JP); Yoshiharu Yamanishi, London (GB); Hachiro Sugimoto, Ibaraki (JP); Yoshio Takeuchi, Toyama (JP); Tetsuo Shibata, Toyama (JP); Emiko Suzuki, Toyama (JP)

(73) Assignee: Eisai Co., Ltd., Tokyo (JP)

( * ) Notice: Subject to any disclaimer, the term of this patent is extended or adjusted under 35 U.S.C. 154(b) by 0 days.

(21) Appl. No.: 09/914,581

(22) PCT Filed: Mar. 2, 2000

(86) PCT No.: PCT/JP00/01232

§ 371 (c)(1),
(2), (4) Date: Aug. 30, 2001

(87) PCT Pub. No.: WO00/51985

PCT Pub. Date: Sep. 8, 2000

(30) Foreign Application Priority Data

Mar. 3, 1999 (JP) .............................. 11-55755

(51) Int. Cl.$^7$ ...................... A61K 31/33; A61K 31/335; C07D 211/06; C07D 401/02; C07D 239/70

(52) U.S. Cl. ...................... 514/183; 514/333; 514/467; 514/682; 514/679; 546/195; 546/206; 546/207; 546/281.7; 546/283.7; 546/285; 549/430; 549/492; 544/253

(58) Field of Search ................. 514/183, 333, 514/467, 682, 679; 546/195, 206, 207, 281.7, 283.7, 285; 549/430, 492; 544/253

(56) References Cited

U.S. PATENT DOCUMENTS

| 4,849,431 A | | 7/1989 | Sugimoto et al. ............ 514/331 |
| 5,100,901 A | * | 3/1992 | Sugimoto et al. ............ 514/445 |
| 5,273,974 A | | 12/1993 | Goto et al. ................. 514/221 |
| 6,277,866 B1 | * | 8/2001 | Takeuchi et al. ............ 514/319 |

FOREIGN PATENT DOCUMENTS

| EP | A1229391 | 7/1987 |
| EP | 0 296 560 | 12/1988 |
| EP | A1487071 | 5/1992 |
| EP | 535496 | 4/1993 |
| EP | A1535496 | 4/1993 |
| JP | A4021670 | 1/1992 |
| JP | 4021670 | 1/1992 |
| JP | 7133274 | 5/1995 |
| JP | A7133274 | 5/1995 |
| WO | 9746526 | 12/1997 |
| WO | A9746526 | 12/1997 |

OTHER PUBLICATIONS

Roman GC, PubMed Abstract 12492785, also cited as Acta Neurol. Scand; 178,6–9(2002),"Defining Dementia . . . ".*
Erkinjuntti et al, PubMed Abstract 12567331, also cited as Semin Clin Neuropsychiatry, 8/1,37–45(2003),"Vascular dementia".*
Markstein R.PubMed Abstract 2575520, also cited as Eur-.Neurol, 29/3,33–41(1989),"Pharmacological approaches in the treatment of SD".*
Trowbridge et al, Pub Med Abstract 12503981, also cited as JAM<A, 289/1, 80–6(2003),"Does this patient have acute cholecystitis?".*

* cited by examiner

Primary Examiner—Mukund J. Shah
Assistant Examiner—Sudhaker B. Patel
(74) Attorney, Agent, or Firm—Birch, Stewart, Kolasch & Birch, LLP

(57) ABSTRACT

The present invention provides a novel compound having an excellent acetylcholinesterase inhibitory effect. That is, it provides a 4-substituted piperidine compound fluoride represented by the following formula, a pharmaceutically acceptable salt thereof or hydrates thereof (provided that 1-benzyl-4-[(5,6-dimethoxy-2-fluoro-1-indanon)-2-yl] methylpiperidine, a pharmaceutically acceptable salt thereof and hydrates thereof are excluded).

(I)

$$R^1 \text{—} \bigcirc \text{—} N \text{—} R^2$$

wherein $R^1$ and $R^2$ represent substituents.

17 Claims, No Drawings

FLUORIDES OF 4-SUBSTITUTED PIPERIDINE DERIVATIVES

This application is the national phase under 35 U.S.C. §371 of PCT International Application No. PCT/JP00/01232 which has an International filing date of Mar. 2, 2000, which designated the United States of America.

TECHNICAL FIELD

The present invention relates to a novel compound useful as a medicament, specifically as an acetylcholinesterase inhibitor, more specifically as an agent for preventing, treating or ameliorating various types of senile dementia, cerebrovascular dementia or attention deficit hyperactivity disorder (ADHD), and further specifically as an agent for preventing, treating and ameliorating various senile dementia especially Alzheimer-type senile dementia, and to a process for producing it.

PRIOR ART

With a rapidly increasing population of the older generation, it is strongly desired to establish a method of treating senile dementia such as Alzheimer-type senile dementia, cerebrovascular dementia and attention deficit hyperactivity disorder.

Development of treating agents for these diseases has been studied from various points of view, and in a prominent point of view, development of acetylcholine precursors and acetylcholinesterase inhibitors is proposed because these diseases are accompanied by a reduction in cholinergic functions in the brain, and actually, such compounds are clinically applied. Typical acetylcholinesterase inhibitors include donepezil hydrochloride (1-benzyl-4-[(5,6-dimethoxy-1-indanon)-2-yl]methylpiperidine hydrochloride), rivastigmine (3-[1-(dimethylamino)ethyl] phenyl N-ethyl-N-methylcarbamate), metrifonate (dimethyl 2,2,2-trichloro-1-hydroxyethyl)phosphate), tacrine hydrochloride (1,2,3,4-tetrahydro-9-acridinamine), galanthamine hydrobromide, neostigmine, physostigmine etc.

However, among these medicaments, denepezil hydrochloride is only the compound that is confirmed to have a pharmaceutical effect on the diseases in actual clinical application and is recognized to have satisfactory usefulness from the viewpoint of side effects and frequency of administration. The other medicaments have some drawbacks such as poor effects, undesirable side effects, necessity for frequent administration per day, and limited use in an injection because of their inapplicability to oral administration. Therefore, there is no or little choice but to choose denepezil hydrochloride at present. As mentioned above, denepezil hydrochloride is a superior medicament. It is needless to say, however, that the presence of acetylcholinesterase inhibitors having more superior effects would be more preferred for a wider choice of medicaments in clinical application. Accordingly, the object of the present invention is to provide a novel compound useful as a medicament, specifically as an acetylcholinesterase inhibitor, more specifically as an agent for preventing, treating or ameliorating various types of senile dementia, cerebrovascular dementia and attention deficit hyperactivity disorder, and further specifically as an agent for preventing, treating or ameliorating Alzheimer-type senile dementia, and a process for producing it.

DISCLOSURE OF THE INVENTION

The present inventors have extensively studied on various compounds for a long period of time for the development of medicaments having more superior effects and higher safety. As a result, they have found that a novel 4-substituted piperidine compound fluoride represented by the following formula (I), a pharmaceutically acceptable salt thereof or hydrates thereof (provided that 1-benzyl-4-[(5,6-dimethoxy-2-fluoro-1-indanon)-2-yl]methylpiperidine, a pharmaceutically acceptable salt thereof and hydrates thereof are excluded) can achieve the above object, and have completed the present invention.

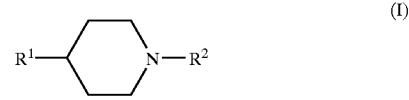

In the formula, $R^1$ represents any one selected from the group consisting of the following substituents:

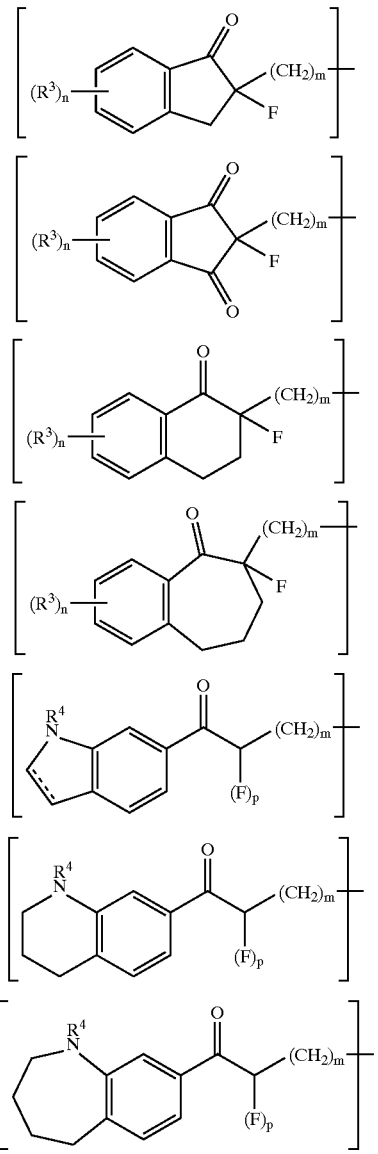

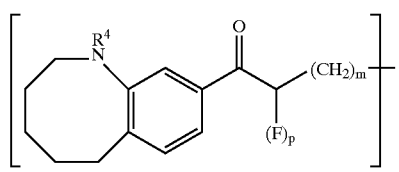
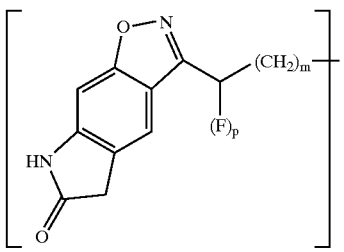
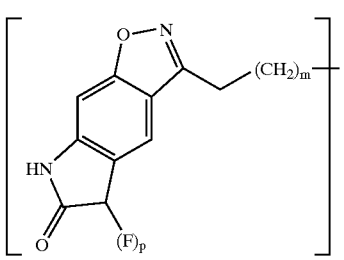
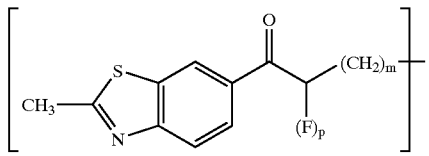
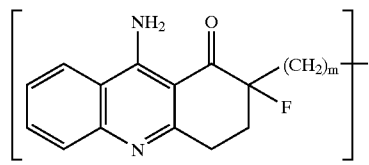
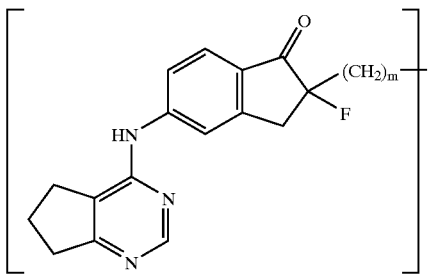
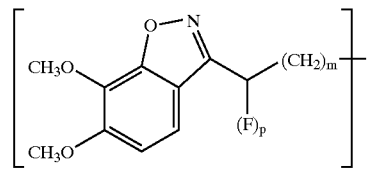
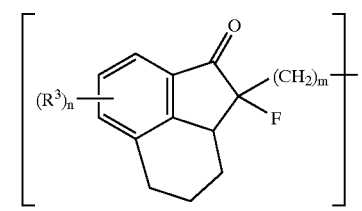

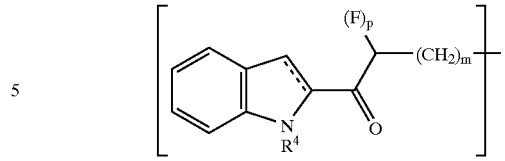

(wherein each $R^3$ are the same as or different from each other and each represents hydrogen atom, a halogen atom, hydroxyl group, a $C_{1-6}$ alkyl group, a C3cycloalkyl group, a $C_{1-6}$ alkoxy group, a $C_{1-6}$ alkoxyalkoxy group, a halogeno $C_{1-6}$ alkyl group, a hydroxy $C_{1-6}$ alkyl group, a cyano $C_{1-6}$ alkyl group, a halogeno $C_{1-6}$ alkoxy group, a hydroxy $C_{1-6}$ alkoxy group, a cyano $C_{1-6}$ alkoxy group, a lower acyl group, a nitro group, an optionally substituted amino group, an optionally substituted amide group, mercapto group or a $C_{1-6}$ thioalkoxy group; $R^4$ represents hydrogen atom or a $C_{1-6}$ alkyl group; the bond represented by the following formula:

=== is a single or double bond; m is 0 or an integer of 1 to 6; n is an integer of 1 to 4; and p is an integer of 1 or 2); and $R^2$ represents a $C_{3-8}$ cycloalkylmethyl group, 2,2-(alkylenedioxy)ethyl group or a group represented by the formula:

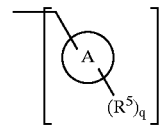

(wherein the ring A is benzene ring or a heterocyclic ring; each $R^1$ are the same as or different from each other and each represents hydrogen atom, a halogen atom, hydroxyl group, nitrile group, a $C_{1-6}$ alkyl group, a $C_{3-8}$ cycloalkyl group, a $C_{1-6}$ alkoxy group, a $C_{1-6}$ alkoxyalkoxy group, an aryloxy group, an aralkyloxy group, a halogeno $C_{1-6}$ alkyl group, a hydroxy $C_{1-6}$ alkyl group, a cyano $C_{1-6}$ alkyl group, a halogeno $C_{1-6}$ alkoxy group, a hydroxy $C_{1-6}$ alkoxy group, a cyano $C_{1-6}$ alkoxy group, a lower acyl group, a nitro group, an optionally substituted amino group, an optionally substituted amide group, mercapto group or a $C_{1-6}$ thioalkoxy group, and two of the $R^5$ groups may together form an aliphatic ring, an aromatic ring, a heterocyclic ring or an alkylenedioxy ring; and q is 0 or an integer from 1 to 5).

That is, the first aspect of the present invention is:
1) a 4-substituted piperidine compound fluoride represented by the above formula (I), a pharmaceutically acceptable salt thereof or hydrates thereof;
2) in the above 1), $R^1$ may be a group represented by the formula:

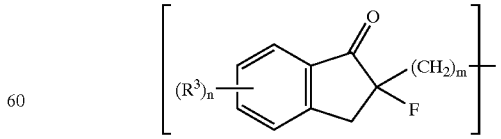

wherein $R^3$, m and n have the same meanings as defined above;

(3) in the above 1), $R^2$ may be a group represented by the formula:

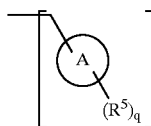

wherein $R^5$ and q have the same meanings as defined above;

4) in the above 3), the ring A may be a group represented by the formula:

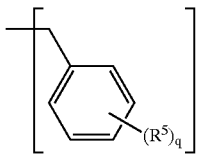

wherein $R^5$ and q have the same meanings as defined above;

5) in the above 3), the ring A may be an aromatic heterocyclic ring;

6) in the above 3), the ring A may be pyridine ring;

7) in the above items 1) to 6), q may be an integer of 1 or 2; and 8) in the above 1), the 4-substituted piperidine compound fluoride may be the one selected from:

(1) 1-benzyl-4-[(5,6-diethoxy-2-fluoro-1-indanon)-2-yl]methylpiperidine;

(2) 1-benzyl-4-[(5,6-dimethoxy-2-fluoro-1-indanon)-2-yl)piperidine;

(3) 1-benzyl-4-[2-[(5,6-dimethoxy-2-fluoro-1-indanon)-2-yl]ethyl]piperidine;

(4) 4-[(5,6-dimethoxy-2-fluoro-1-indanon)-2-yl]methyl-1-(3-fluorobenzyl)piperidine;

(5) 4-[(5,6-dimethoxy-2-fluoro-1-indanon)-2-yl]methyl-1-(3-methylbenzyl)piperidine;

(6) 1-cyclohexylmethyl-4-[(5,6-dimethoxy-2-fluoro-1-indanon)-2-yl]methylpiperidine;

(7) 4-[(5,6-dimethoxy-2-fluoro-1-indanon)-2-yl]methyl-1-(1,3-dioxolan-2-yl)methylpiperidine; and (8) 1-(4-benzyloxybenzyl)-4-[(5,6-dimethoxy-2-fluoro-1-indanon)-2-yl]methylpiperidine;

(9) 3-(1-benzylpiperidin-4-yl)-2-fluoro-1-(2,3,4,5-tetrahydro-1H-1-benzazepin-8-yl)-1-propanone;

(10) 3-(1-benzylpiperidin-4-yl)-2,2-difluoro-1-(2,3,4,5-tetrahydro-1H-1-benzazepin-8-yl)-1-propanone;

(11) 5,7-dihydro-3-[1-fluoro-2-[1-phenylmethyl]-4-piperidinyl]ethyl]-6H-pyrolo[4,5-f]-1,2-benzisooxasol-6-on;

(12) 5,7-dihydro-3-[1,1-difluoro-2-[1-phenylmethyl]-4-piperidinyl]ethyl]-6H-pyrolo[4,5-f]-1,2-benzisooxasol-6-on;

(13) 1-(2-methyl-6-benzothiazoryl)-3-[1-phenylmethyl]-4-piperidinyl]-2-fluoro-1-propanone; and

(14) 1-(2-methyl-6-benzothiazoryl)-3-[1-phenylmethyl]-4-piperidinyl]-2,2-difluoro-1-propanone.

The second aspect of the present invention is:

9) a pharmaceutical preparation comprising, as an active ingredient, the 4-substituted piperidine compound fluoride of the above 1), a pharmaceutically acceptable salt thereof or hydrates thereof;

10) in the above 9), the pharmaceutical preparation may be an acetylcholinesterase inhibitor;

11) in the above 9), the pharmaceutical preparation may be an agent for treating, preventing or ameliorating various types of senile dementia, cerebrovascular dementia or attention deficit hyperactivity disorder; and 12) in the above 11), the various types of senile dementia may be Alzheimer-type senile dementia.

That is, the present invention provides a method for preventing, treating or ameliorating a disease against which acetylcholinesterase inhibition is effective and a method for preventing, treating or ameliorating various types of senile dementia, cerebrovascular dementia or attention deficit hyperactivity disorder, by administering a pharmaceutically effective amount of the above pharmaceutical preparation to a patient. The present invention also provides use of the 4-substituted piperidine derivative fluoride, a pharmaceutically acceptable salt thereof or hydrates thereof for producing the above pharmaceutical preparations and a pharmaceutical composition comprising it.

The third aspect of the present invention is:

13) a process for producing the 4-substituted piperidine compound fluoride as described in the above 1), a pharmaceutically acceptable salt thereof or hydrates thereof (provided that 1-benzyl-4-[(5,6-dimethoxy-2-fluoro-1-indanon)-2-yl]methylpiperidine, a pharmacologically acceptable salt thereof and hydrates thereof are excluded), which comprises fluorinating the 4-substituted piperidine compound represented by the following formula (II); and, if required, converting it into a salt.

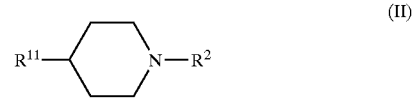

(II)

In the formula, $R^{11}$ represents any group selected from the following substituents:

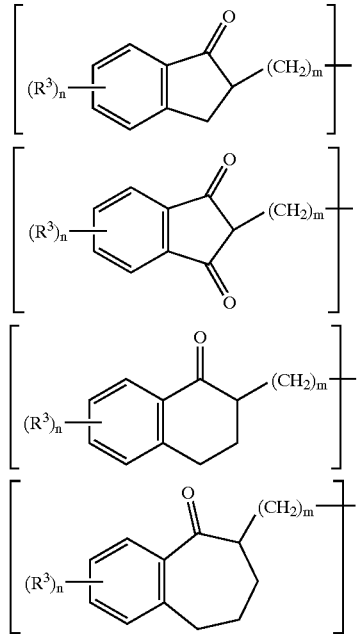

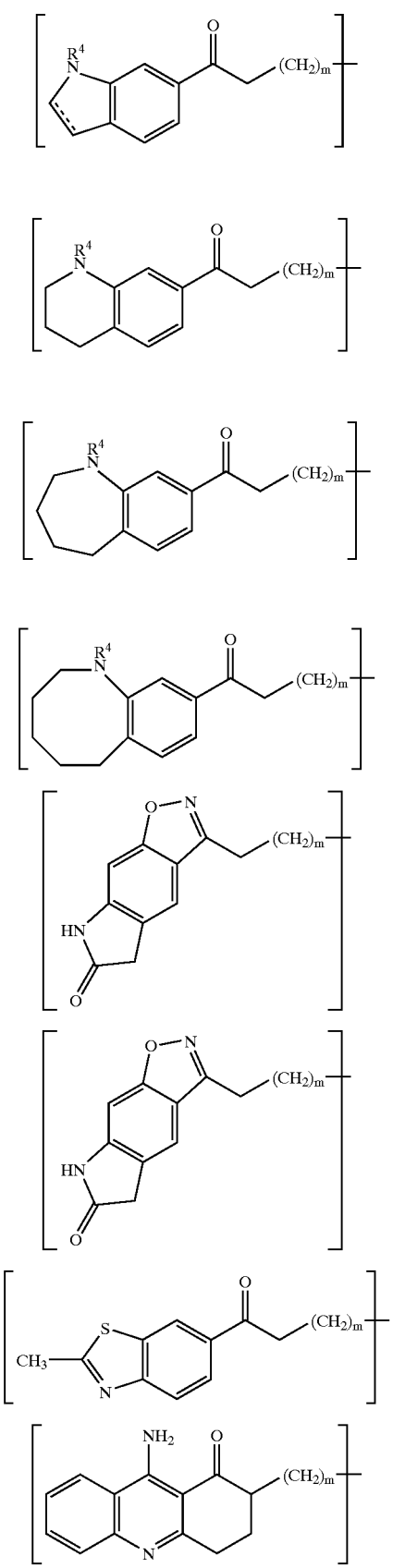

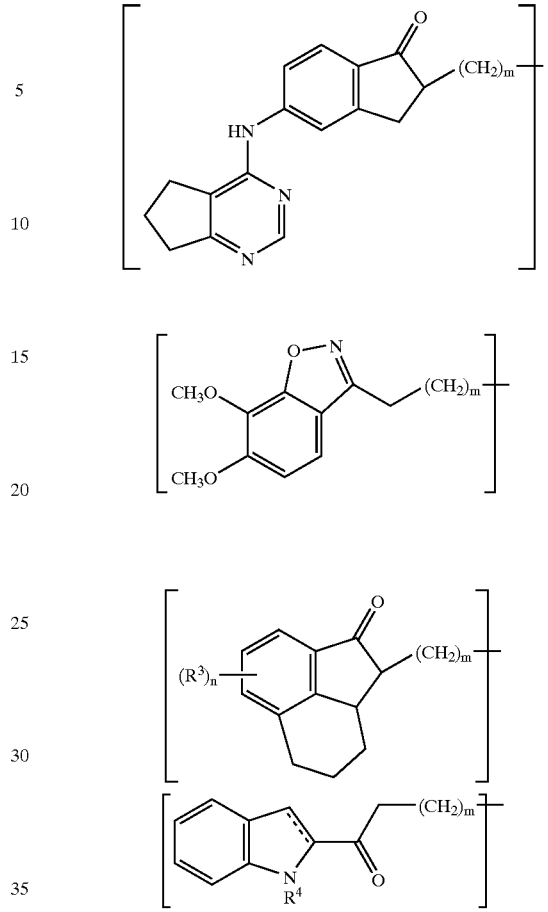

(wherein $R^3$, $R^4$, n, m, p and the bond represented by the following formula:

═══ have the same meanings as defined; and $R^2$ has the same meanings as defined above.

Further, 14) in the process of the above 13), the flourinating agent may be N-flourobenzenesufonimide, 3-cyclohexyl-2-flouro-2,3-dihydro-3-methyl-1,1-dioxide-1,2-benzisothiazole or 2-flouro-3,3-dimethyl-2,3-dihydro-1,2-benzisothiazole-1,1-dioxide.

Hereinafter, the symbols, terms etc. used in the present specification are explained and the present invention is illustrated in more detail.

In the specification of the present invention, the chemical structure of the compound may represent a certain isomer or isotope for convenience. However, the present invention involves all isomers (e.g., genometric isomers, optical isomers based on asymmetric carbon atoms, stereoisomers and tautomers), isomeric mixtures and isotopes which may structurally occur. Accordingly, the compound of the present invention is not limited to that described in the formula of convenience, and may be one of or a mixture of the isomers or one of the isotopes. Therefore, in the compound of the present invention, although an asymmetric carbon atom may be included in the molecule and there may occur optically active forms and racemates, the compound of the present invention is not particularly limited to a certain form and may include any of such forms. In addition, various type of crystal polymorphism may also occur. However, the compound of the present invention is not also limited to a certain type of polymorphism and may have a single crystalline morphology or a mixture of two or more types of crystalline morphology and may be in the form of an anhydride or a hydrate.

Definition of $R^1$

In the formula (I) above, $R^1$ represents any group selected from the the substituents represented by the following formulae, provided that such a substituent is excluded that provides 1-benzyl-4-[(5,6-dimethoxy-1-indanon)-2-yl] methylpiperidine as the 4-substituted piperidine compound fluoride represented by the formula (I).

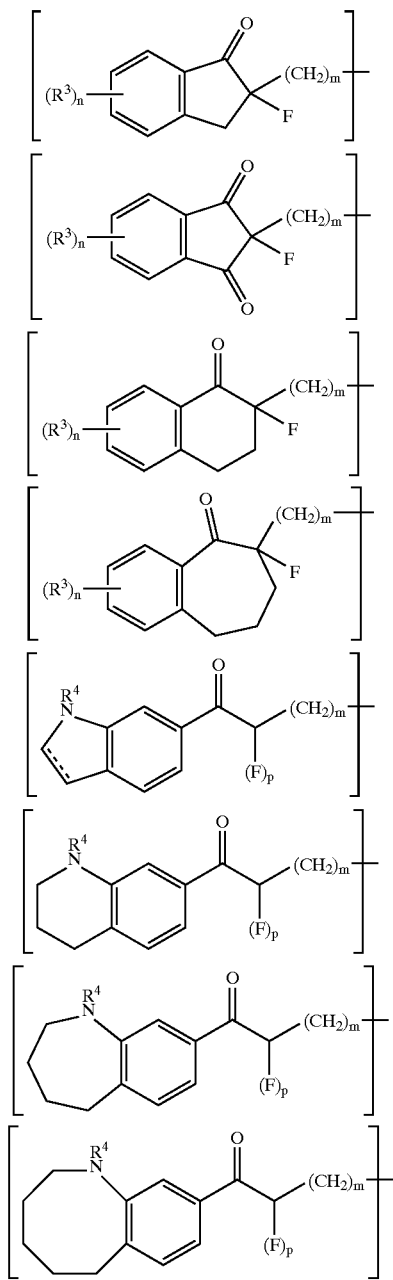

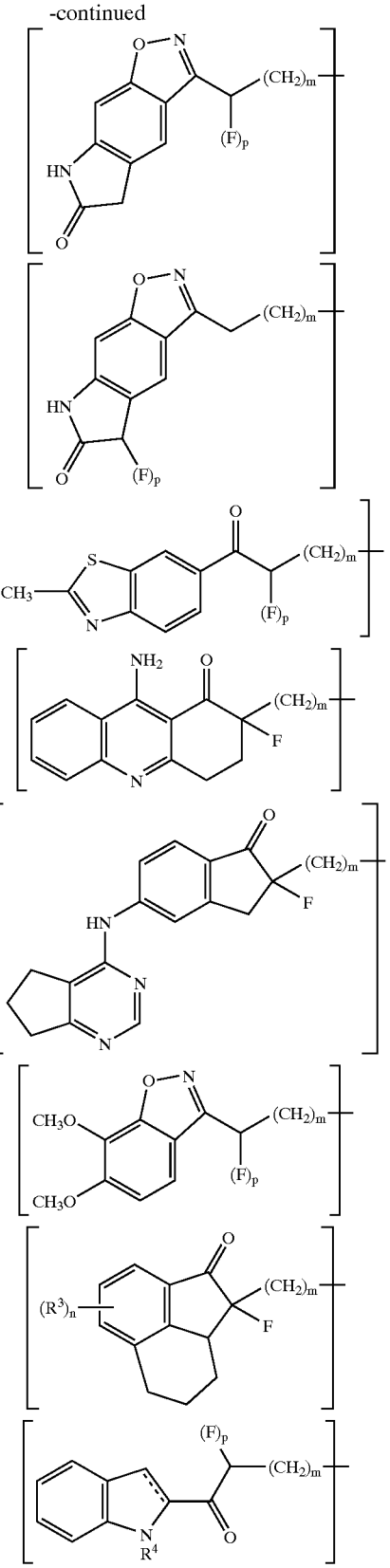

In the formula, each $R^3$ are the same as or different from each other and each represents hydrogen atom, a halogen atom, hydroxyl group, a $C_{1-6}$ alkyl group, a $C_{3-8}$ cycloalkyl group, a $C_{1-6}$ alkoxy group, a $C_{1-6}$ alkoxyalkoxy group, a halogeno $C_{1-6}$ alkyl group, a hydroxy $C_{1-6}$ alkyl group, a cyano $C_{1-6}$ alkyl group, a halogeno $C_{1-6}$ alkoxy group, a hydroxy $C_{1-6}$ alkoxy group, a cyano $C_{1-6}$ alkoxy group, a lower acyl group, a nitro group, an optionally substituted amino group, an optionally substituted amide group, mercapto group or a $C_{1-6}$ thioalkoxy group;

$R^4$ represents hydrogen atom or a $C_{1-6}$ alkyl group;

the bond represented by the following formula:

represents a single or double bond;

m is 0 or an integer of 1 to 6;

n is an integer of 1 to 4; and p is an integer of 1 or 2.

The "halogen atom" represented by the above $R^3$ refers to, for example, fluorine, chlorine, bromine or iodine, preferably fluorine, chlorine or bromine.

The "$C_{1-6}$ alkyl group" represented by the above $R^3$ or $R^4$ refers to an alkyl group having 1 to 6 carbon atoms, including a linear or branched alkyl groups such as methyl, ethyl, n-propyl, i-propyl, n-butyl, i-butyl, t-butyl, n-pentyl, i-pentyl, neopentyl, hexyl, 1-methylpropyl, 1-methylbutyl and 2-methylbutyl groups.

The "$C_{3-8}$ cycloalkyl group" represented by the above $R^3$ refers to a cyclic alkyl group having 3 to 8 carbon atoms, such as cyclopropy, cyclobutyl, cyclopentyl, cyclohexyl, cycloheptyl and cyclooctyl groups.

The "$C_{1-6}$ alkoxy group" represented by the above $R^3$ refers to a group in which a "$C_{1-6}$ alkyl group" as defined above is bonded to an oxygen atom, and includes a linear or branched alkoxy groups such as methoxy, ethoxy, n-propoxy, i-propoxy, n-butoxy, i-butoxy, t-butoxy, pentyloxy and hexyloxy groups.

The "$C_{1-6}$ alkoxyalkoxy group" represented by the above $R^3$ refers to a group in which the $C_{1-6}$ alkoxy group as defined above is bound to another "$C_{1-6}$ alkoxy group", such as methoxymethoxy, methoxyethoxy, methoxypropoxy, ethoxymethoxy, ethoxyethoxy, ethoxypropoxy and propoxypropoxy groups.

The "halogeno $C_{1-6}$ alkyl group" represented by the above $R^3$ refers to a group in which 1 or more of the same or different halogen atoms are bonded to the "$C_{1-6}$ alkyl group" having the same meaning as defined above, such as chloromethyl, dichloromethyl, trichloromethyl, fluoromethyl, difluoromethyl, trifluoromethyl, fluoroethyl, difluoroethyl and trifluoroethyl.

The "hydroxy $C_{1-6}$ alkyl group" represented by the above $R^3$ refers to a group in which one or more hydroxyl groups are bonded to the $C_{1-6}$ alkyl group as defined above, such as hydroxymethyl, hydroxyethyl and 2,3-hydroxypropyl.

The "cyano $C_{1-6}$ alkyl group" represented by the above $R^3$ refers to a group in which one or more cyano groups are bonded to the $C_{1-6}$ alkyl group as defined above, such as cyanomethyl, cyanoethyl and cyanopropyl groups.

The "halogeno $C_{1-6}$ alkoxy group" represented by the above $R^3$ refers to a group in which an oxygen atom is bonded to the "halogeno $C_{1-6}$ alkyl group" as defined above; the "hydroxy $C_{1-6}$ alkoxy group" represented by the above $R^3$ refers to a group in which an oxygen atom is bonded to the "hydroxy $C_{1-6}$ alkyl group" as defined above; and the "cyano $C_{1-6}$ alkoxy group" represented by the above $R^3$ refers to a group in which an oxygen atom is bonded to the "cyano $C_{1-6}$ alkyl group" as defined above.

The "lower acyl group" represented by the above $R^3$ refers to a linear or branched acyl group derived from a fatty acid having 1 to 6 carbon atoms, such as formyl, acetyl, propionyl, butyryl, isobutyryl, valeryl, isopvaleryl, pivaloyl and hexanoyl groups.

The "optionally substituted amino group which may be substituted" represented by the above $R^3$ refers an amino group in which the nitrogen atom may be substituted by a group such as a $C_{1-6}$ alkyl group, including cyclic amino groups. Examples of the "optionally substituted amino group" include amino (—$NH_2$), methylamino (—$NHCH_3$), diemthylamino (—$N(CH_3)_2$), pyrrolidinyl, pyrazolinyl, piperidinyl and piperazinyl groups.

The "optionally substituted amide group" represented by the above $R^3$ refers to an amide group in which the nitrogen atom may be substituted by a group such as a $C_{1-6}$ alkyl group, including amide groups of cyclic amines. Examples of the "optionally substituted amide group" include amide (—$CONH_2$), N-methylamide (—$CONHCH_3$), N,N-dimethylamide (—$CON(CH_3)_2$), N-ethylamide (—$CONHC_2H_5$), N,N-diethylamide (—$CON(C_2H_5)_2$), N-methyl-N-ethylamide (—$CON(CH_3)C_2H_5$), pyrrolidinylcarbonyl, pyrazolinylcarbonyl, piperidinylcarbonyl and piperazinylcarbonyl groups.

The "$C_{1-6}$ thioalkoxy group" represented by the above $R^3$ refers to a group in which the $C_{1-6}$ alkyl group as defined above is bonded to a sulfur atom, such as methylthio (—$SCH_3$) and ethylthio (—$SC_2H_5$) groups.

In $R^1$ of the above formula (I), the symbol "m" is 0 or an integer from 1 to 6, preferably 0 or an integer from 1 to 5, more preferably 0 or an integer from 1 to 3, still more preferably 0 or an integer of 1 or 2, most preferably 0 or 1. The symbol "n" is an integer from 1 to 4, preferably an integer from 1 to 3, more preferably an integer of 1 or 2. The symbol "p" is an integer of 1 or 2, preferably 1.

In the formula (I), $R^1$ is preferably a group represented by the formula:

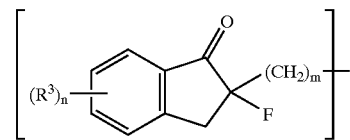

wherein $R^3$, m and n have the same meanings as defined above. In this case, it is more preferred that $R^1$ be hydrogen atom, a halogen atom, hydroxyl group, a $C_{1-6}$ alkyl group, a $C_{1-6}$ alkoxy group, a halogeno $C_{1-6}$ alkyl group, a hydroxy $C_{1-6}$ alkyl group, a cyano $C_{1-6}$ alkyl group, a halogeno $C_{1-6}$ alkoxy group, a hydroxy $C_{1-6}$ alkoxy group or a cyano $C_{1-6}$ alkoxy group; and m be 0 or an integer from 1 to 5. It is still more preferred that $R^3$ be hydrogen atom, a $C_{1-6}$ alkoxy group, a halogeno $C_{1-6}$ alkyl group, a halogeno $C_{1-6}$ alkoxy group, a hydroxy $C_{1-6}$ alkoxy group or a cyano $C_{1-6}$ alkoxy group; and m be 0 or an integer from 1 to 3. It is most preferred that $R^3$ be hydrogen atom or a $C_{1-6}$ alkoxy group (such as methoxy, ethoxy, n-propoxy and i-propoxy group); and m be 0, 1 or 2.

Definition of $R^2$

In the formula (I), $R^2$ represents a $C_{3-8}$ cycloalkylmethyl group, 2,2-(alkylenedioxy)ethyl group or a group represented by the following formula:

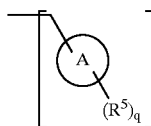

(wherein the ring A is benzene ring or a heterocyclic ring; each $R^1$ are the same as or different from each other and each represents hydrogen atom, a halogen atom, hydroxyl group, nitrile group, a $C_{1-6}$ alkyl group, a $C_{3-8}$ cycloalkyl group, a $C_{1-6}$ alkoxy group, a $C_{1-6}$ alkoxyalkoxy group, an aryloxy group, an aralkyloxy group, a halogeno $C_{1-6}$ alkyl group, a hydroxy $C_{1-6}$ alkyl group, a cyano C1alkyl group, a halogeno $C_{1-6}$ alkoxy group, a hydroxy $C_{1-6}$ alkoxy group, a cyano $C_{1-6}$ alkoxy group, a lower acyl group, nitro group, an optionally substituted amino group, an optionally substituted amide group, mercapto group or a $C_{1-6}$ thioalkoxy group and two of the $R^5$ groups may together form an aliphatic ring, an aromatic ring, a heterocyclic ring or an alkylenedioxy ring; and q is 0 or an integer from 1 to 5), provided that such a $R^2$ group is excluded that provides 1-benzyl-4-[(5,6-dimethoxy-1-indanon)-2-yl]methylpiperidine as the 4-substituted piperidine compound fluoride.

The "$C_{3-8}$ cycloalkyl group" in the "$C_{3-8}$ cycloalkylmethyl group" represented by the above $R^2$ refers to the $C_{3-8}$ cycloalkyl group as defined above, and the "$C_{3-8}$ cycloalkylmethyl group" refers to a group in which the $C_{3-8}$ cycloalkyl group is bonded to methyl group. Examples include cyclopropylmethyl, cyclobutylmethyl, cyclopentylmethyl, cyclohexylmethyl, cycloheptylmethyl and cyclooctylmethyl groups. Among these, cyclohexylmethyl group is more preferred.

The "2,2-(alkylenedioxy)ethyl group" represented by the above $R^2$ refers to a group in which the terminal carbon atom of an ethyl group is substituted by a cyclic alkylenedioxy group (i.e., an acetal group), such as 2,2-(ethylenedioxy)ethyl (also referred to as 1,3-dioxolan-2-yl]methyl), 2,2-(propylenedioxy)ethyl (also referred to as 1,3-dioxan-2-yl)methyl) and 2,2-(butylenedioxy)ethyl (also referred to as 1,3-dioxepan-2-yl)methyl) groups. Among these groups, 2,2-(ethylenedioxy)ethyl group is more preferred.

The "aryl group" in the "aryloxy group" represented by the above $R^5$ refers to a cyclic hydrocarbon group forming an aromatic ring structure, including those of mono-, di- and tri-cyclic types, such as phenyl, indenyl, naphthyl, azlenyl, heptalenyl, anthnyl and phenanthrenyl groups. The "aryloxy group" refers to a group in which the aryl group is bound to an oxyge atom, such as phenoxy and naphthyloxy groups.

The "aralkyloxy group" represented by the above $R^5$ refers to a group in which the aryl group as defined above is bound to a $C_{1-6}$ alkyl group and the resulting arylalkyl group is further bound to an oxygen atom, such as benzyloxy, phenylethoxy, phenylpropoxy and naphthylmethoxy groups.

The "halogen atom", "$C_{1-6}$ alkyl group", "$C_{3-8}$ cycloalkyl group", "$C_{1-6}$ alkoxy group", "$C_{1-6}$ alkoxyalkoxy group", "halogeno $C_{1-6}$ alkyl group", "hydroxy $C_{1-6}$ alkyl group", "cyano $C_{1-6}$ alkyl group", "halogeno $C_{1-6}$ alkoxy group", "hydroxy $C_{1-6}$ alkoxy group", "cyano $C_{1-6}$ alkoxy group", "lower acyl group", "an optionally substituted amino group", "an optionally substituted amide group" and "$C_{1-6}$ thioalkoxy group" represented by the above $R^5$ have the same definitions as those for the above halogen atom, $C_{1-6}$ alkyl group, $C_{3-8}$ cycloalkyl group, $C_{1-6}$ alkoxy group, $C_{1-6}$ alkoxyalkoxy group, halogeno $C_{1-6}$ alkyl group, hydroxy $Cl_6$ alkyl group, cyano $C_{1-6}$ alkyl group, halogeno $C_{1-6}$ alkoxy group, hydroxy $C_{1-6}$ alkoxy group, cyano $C_{1-6}$ alkoxy group, lower acyl group, an optionally substituted amino group, an optionally substituted amide group and $C_{1-6}$ thioalkoxy group, respectively. The "$C_{1-6}$ alkoxycarbonyl group" refers to a group in which the $C_{1-6}$ alkoxy group as defined above is bound to a carbonyl group, such as methoxycarbonyl ($—COOCH_3$) and ethoxycarbonyl ($—COOC_2H_5$) groups.

In the above definition for R5, two $R^5$ groups may together form an aliphatic ring, such as cyclopentane, cyclohexane, cycloheptane and cyclooctane rings; may together form an aromatic ring, such as benzene ring; may together form a heterocyclic ring, such as furan, thiophene, pyrrole, imidazole, oxazole, thizole, triazole, pyridine, pyrazine, pyrimidine, tetrahydrofuran, tetrahydropyran, dioxane, dioxolane, piperidine, piperazine, morpholine and thiomorpholine rings; and may together form an alkylenedioxy ring, such as methylenedioxy, ethylenedioxy and propylenedioxy groups.

In the above $R^2$, the "heterocyclic ring" represented by the ring A refers to a ring having 1 to 4 hetero atoms such as nitrogen, sulfur and oxygen atoms, including a "5- to 14-membered aromatic heterocyclic ring" and a "5- to 10-membered non-aromatic heterocyclic ring".

1) As the "5- to 14-membered aromatic heterocyclic ring", there may be mentioned, for example, a mono-, di- or tri-cyclic, 5- to 14-membered aromatic heterocyclic ring having 1 to 4 atoms selected from the group consisting of nitrogen, sulfur and oxygen atoms, including: (1) nitrogen-containing aromatic heterocyclic rings such as pyrrole, pyridine, pyridazine, pyrimidine, pyrazine, pyrazole, imidazole, indole, isoindole, indolidine, purine, indazole, quinoline, isoquinoline, quinolizine, phthalazine, naphthyridine, quisoxaline, quinazoline, cinnoline, pteridine, imidazotriazine, pirazinopyridazine, acridine, phenanthridine, carbazole, carbazoline, perimidine, phenanthroline and phenasine rings; (2) sulfur-containing aromatic heterocyclic rings, such as thiophene and benzothiophene rings; (3) oxygen-containing aromatic haterocyclic rings, such as furan, pyran, cyclopentapyran, benzofuran and isobenzofuran rings; and (4) aromatic heterocyclic rings containing two or more different atoms selected from nitrogen, sulfur and oxygen atoms, such as thiazole, isothiazole, benzthiazole, benzthiadiazole, phenothiazine, isoxazole, furazan, phenoxazine, pyrazoloxazole, imidazothiazole, thienofuran, furopyrrole and pyridoxadine rings.

2) The "5- to 10-membered non-aromatic heterocyclic ring" refers to a hydrocarbon ring in which 1 to 4 carbon atoms are substituted by heteroatoms selected from nitrogen, sulfur and oxygen atoms, including unsaturated fused rings. Examples of the "5- to 10-membered non-aromatic heterocyclic ring" include pyrrolidine, pyrroline, piperidine, piperazine, imidazoline, pyrazolidine, imidazolidine, morpholine, tetrahydropyran, aziridine, oxirane and oxathiorane rings and phthalimide and succinimide.

3) The ring A is preferably benzene, pyridine, pyridazine, pyrimidine, pyrazine, piperidine, piperadine or morpholine ring.

In the formula (I) above, $R^2$ is preferably a $C_{3-8}$ cycloalkylmethyl group or a group represented by the formula:

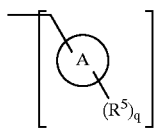

(wherein the ring A, $R^5$ and q have the same meanings as defined above), more preferably a group represented by the formula:

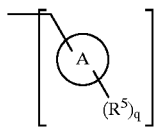

(wherein the ring A, $R^5$ and q have the same meanings as defined above), and still more preferably a group represented by the formula:

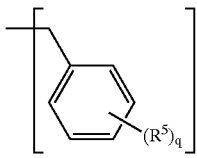

(wherein $R^5$ and q have the same meanings as defined above) provided that such a $R^2$ group is excluded that provides 1-benzyl-4-[(5,6-dimethoxy-1-indanon)-2-yl] methylpiperidine as the 4-substituted piperidine compound fluoride represented by the formula (I).

$R^1$ and $R^2$ in the formula (I) are defined as described above. In the formula (I), each of $R^1$ and $R^2$ can be selected independently from the groups in the definition, respectively, and it goes without saying that $R^1$ and $R^2$ are not limited to a certain combination (provided that such a combination is excluded that provides 1-benzyl-4-[(5,6-dimethoxy-1-indanon)-2-yl]methylpiperidine). The most preferred embodiments of the compound according to the present invention include the following compounds, a salt thereof or hydrates thereof, but it goes without saying that the present invention is not limited to them:

(1) 1-benzyl-4-[(5,6-diethoxy-2-fluoro-1-indanon)-2-yl] methylpiperidine;
(2) 1-benzyl-4-[(5,6-dimethoxy-2-fluoro-1-indanon)-2-yl]piperidine;
(3) 1-benzyl-4-[2-[(5,6-dimethoxy-2-fluoro-1-indanon)-2-yl]ethyl]piperidine;
(4) 4-[(5,6-dimethoxy-2-fluoro-1-indanon)-2-yl]methyl-1-(3-fluorobenzyl)piperidine;
(5) 4-[(5,6-dimethoxy-2-fluoro-1-indanon)-2-yl]methyl-1-(3-methylbenzyl)piperidine;
(6) 1-cyclohexylmethyl-4-[(5,6-dimethoxy-2-fluoro-1-indanon)-2-yl]methylpiperidine;
(7) 4-[(5,6-dimethoxy-2-fluoro-1-indanon)-2-yl]methyl-1-(1,3-dioxolan-2-yl)methylpiperidine;
(8) 1-(4-benzyloxybenzyl)-4-[(5,6-dimethoxy-2-fluoro-1-indanon)-2-yl]methylpiperidine;
(9) 3-(1-benzylpiperidin-4-yl)-2-fluoro-1-(2,3,4,5-tetrahydro-1H-1-benzazepin-8-yl)-1-propanone;
(10) 3-(1-benzylpiperidin-4-yl)-2,2-difluoro-1-(2,3,4,5-tetrahydro-1H-1-benzazepin-8-yl)-1-propanone;
(11) 5,7-dihydro-3-[1-fluoro-2-[1-phenylmethyl]-4-piperidinyl]ethyl]-6H-pyrolo[4,5-f]-1,2-benzisooxasol-6-on;
(12) 5,7-dihydro-3-[1,1-difluoro-2-[1-phenylmethyl]-4-piperidinyl]ethyl)-6H-pyrolo[4,5-f]-1,2-benzisooxasol-6-on;
(13) 1-(2-methyl-6-benzothiazoryl)-3-[1-phenylmethyl]-4-piperidinyl]-2-fluoro-1-propanone; and
(14) 1-(2-methyl-6-benzothiazoryl)-3-[1-phenylmethyl]-4-piperidinyl]-2,2-difluoro-1-propanone.

The "pharmaceutically acceptable salt" as used in the present invention is not particularly limited as long as it is an addition salt formed with the compound of the present invention. Specific examples include: hydroacid salt halides, such as hydrofluorides, hydrochlorides, hydrobromides and hydroiodides; inorganic acid salts, such as sulfates, nitrates, perchlorates, phosphates, carbonates and bicarbonates; organic carboxylic acid salts, such as acetates, oxalates, maleates, tartrates and fumarates; organic sulfonates, such as methane sulfonates, trifluoromethane sulfonates, ethane sulfonates, benzene sulfonates, toluene sulfonates and camphor sulfonates; amino acid salts, such as aspartates and glutamates; salts with an amine, such as trimethylamine salts, triethylamine salts, procaine salts, pyridine salts and phenethylbenzylamine salts; alkali metal salts, such sodium salts and potassium salts; and alkali earth metal salts, such as magnesium salts and calcium salts; preferably hydrochlorides and oxalates.

For the production of the compound of the present invention, various processes may be employed. Typically, the following process is employed. It goes without saying that the compound of the present invention can also be produced by another process.

Florination of 4-Substituted Piperidine Compound

It can be produced by fluorinating the 4-substituted piperidine compound produced according to the process described in, for example, JP-A 64-79151 (EP-296560-A1), JP-A 55-140149 (EP-487071-A1), JP-B 6-500794, JP-B 6-510788, 6-508904, JP-A 5-279355, JP-A 5-320160, JP-A 6-116237 or JP-A 6-41070 and represented by the following formula (II) (provided that 1-benzyl-4-[(5,6-dimethoxy-1-indanon)-2-yl]methylpiperidine is excluded); and, if required, converting it into a salt.

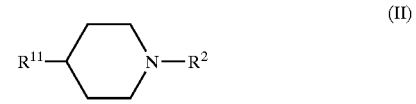

In the formula, "R" represents any group selected from the following substituents:

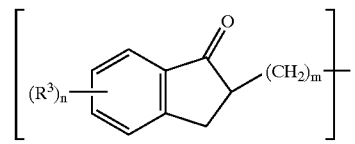

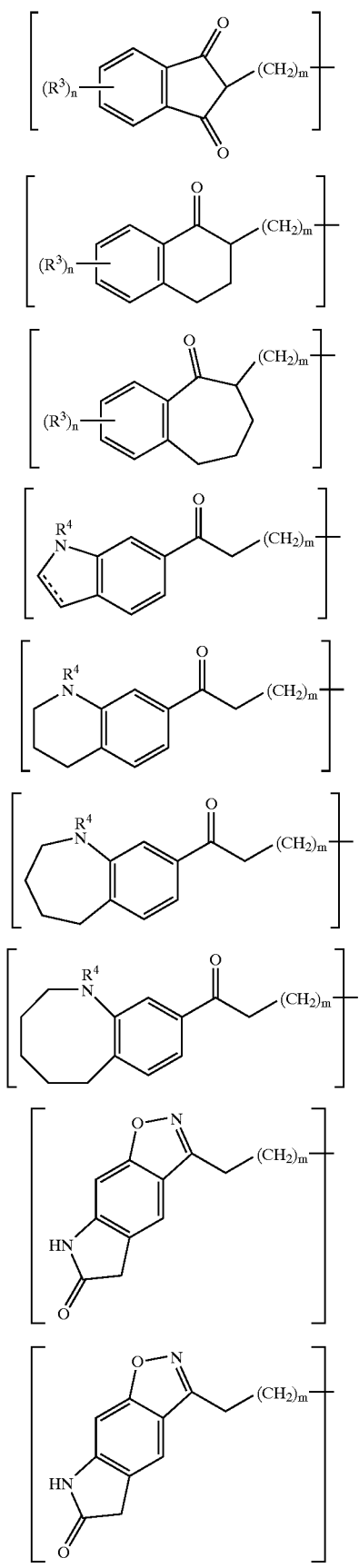
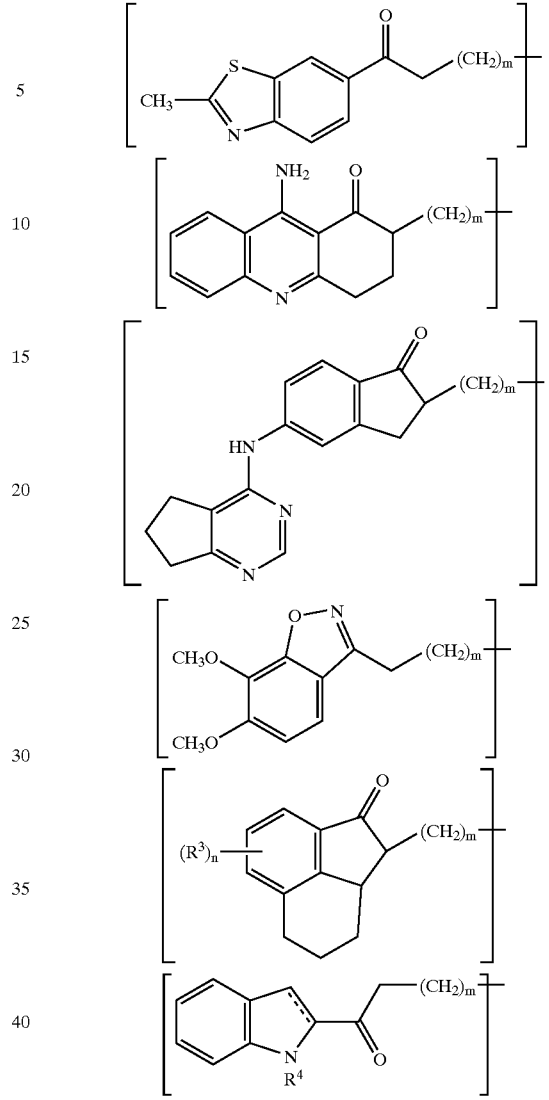

(wherein $R^3$, $R^4$, n, m, p and the bond represented by the following formula:

=== have the same meanings as defined above); and
$R^2$ is has the same meaning as defined above.

In this case, a desirable result can be generally obtained when the starting compound is reacted first with a base and then with a fluorinating gent.

In the production process described above, the base to be used is preferably a strong base, such as lithium bis (trimethylsilyl) amide, n-butyl lithium, lithium diisopropylamide, sodium amide, sodium hydride, sodium methoxide, sodium ethoxide, potassium t-butoxide, sodium hydroxide and potassium hydroxide, and is not particularly limited. The fluorinating agent to be used includes, for example, N-fluorobenzenesulfonimide (NFSI, CAS Registration No: 133745-75-2), 3-cyclohexyl-2-fluoro-2,3-dihydro-3-methyl-1,1-dioxide-1,2-benzisothiazole (CMIT-F, CAS Reg. Nos: 186806-24-6, 196106-79-3), 2-fluoro-3,3-dimethyl-2,3-dihydro-1,2-benzisothiazole-1,1-dioxide (CAS Reg. No: 124170-23-6), diethylaminosulfur trifluoride (DAST, CAS Reg. No: 38078-09-0), N,N-diethyl-1,1,2,3,3,3-hexafluoropropylamine (Ishikawa Reagent), hydrogen fluoride, tetraalkylammonium fluoride, potassium fluoride, cesium fluoride, hydrogen fluoride-pyridine (Olah Reagent) etc. Among these agents, N-fluorobenzenesulfonimide, 3-cyclohexyl-2-fluoro-2,3-dihydro-3-methyl-1,1-dioxide-1,2-benzisothiazole or 2-fluoro-3,3-dimethyl-2,3-dihydro-1,2-benzisothiazole-1,1-dioxide are preferred. The solvent used here is not limited as long as it is inert to the above-mentioned strong bases and fluorinating agents. Specific examples of the solvent include tetrahydrofuran (THF), 1,2-dimethoxyethane (DME; ethylene glycol dimethyl ether), ethyl ether, isopropyl ether, butyl ether, 1,3-dioxane, 1,4-dioxane, 1,3-dioxolane, 1,4-dioxolane, benzene, toluene, xylene, cyclohexane, n-hexane, n-pentane, n-octane and petroleum ether. These solvents may be used singly or as a mixture of two or more of them.

The compound (I) of the present invention can be produced by the process described above. The starting compound in the reaction may in the form of a salt or hydrate, and is not particularly limited as long as it is inert to the reaction. In the case where the compound (I) of the present invention is obtained in a free form, the obtained compound (I) may be converted into a salt which the compound (I) can form by a conventional method. Each of various isomers of the compound (I) of the present invention obtained may be purified and isolated by conventional separation mean (e.g., recrystallization, chromatography, etc.). Particularly in the case where an optically active form of the compound of the present invention is desired, it can be obtained by, for example, any of the following methods.

(1) To use an optically active fluorinating agent.
(2) To resolve racemates optically.

The compound (I) of the present invention may be formulated into tablets, powder, fine granules, granules, coated tablets, capsules, syrup, troche, inhalant, suppository, injection, ointment, ophthalmic ointment, eye drops, nose drops, ear drops, poultice, lotion etc. by a conventional method. In the formulation, there can be used conventional fillers, binders, lubricants, coloring agents and flavoring agents and, if necessary, stabilizing agents, emulsifying agents, absorbefacients, surfactants, pH adjusting agents, preservatives, antioxidants etc. may also be used. In general, the formulation is performed by blending components to used as the raw materials for a pharmaceutical preparation in a conventional manner. For example, for the preparation of for oral administration, the compound of the present invention or a pharmaceutically acceptable salt thereof and a filler and, if necessary, a binder, a disintegrant, a lubricant, a coloring agent, a flavoring agent etc. are blended together, and then formed into powder, fine granules, granules, tablets, coated tablets, capsules or the like in a conventional manner. The components of these additives include, for example, animal and plant oils such as soy bean oil, beef tallow and synthetic glycerides; hydrocarbons such as liquid paraffin, squalane and solid paraffin; ester oils such as octyl dodecyl myristate and isopropyl myristate; higher alcohols such as cetostearyl alcohol and behenyl alcohol; silicone resins; silicone oils; surfactants such as polyoxyethylene fatty acid esters, sorbitan fatty acid esters, glycerol fatty acid esters, polyoxyethylene sorbitan fatty acid esters, polyoxyethylene hardened castor oil and polyoxyethylene/polyoxypropylene block copolymer; water-soluble polymers such as hydroxyethyl cellulose, polyacrylic acid, carboxyvinyl polymer, polyethylene glycol, polyvinyl pyrrolidone and methyl cellulose; lower alcohols such as ethanol and isopropanol; polyhydric alcohols such as glycerol, propyleneglycol, dipropyleneglycol and sorbitol; saccharides such as glucose and saccharose; inorganic powders such as silicic anhydride, magnesium aluminum silicate and aluminum silicate; purified water; etc. The filler to be used includes, for example, lactose, corn starch, saccharose, glucose, mannitol, sorbitol, crystalline cellulose and silicon dioxide; the binder includes, for example, polyvinyl alcohol, polyvinyl ether, methyl cellulose, ethyl cellulose, gum arabic, tragacanth, gelatin, shellac, hydroxypropylmethyl cellulose, hydroxypropyl cellulose, polyvinyl pyrrolidone, polypropylene glycol/polyoxyethylene block polymer and meglumine; the disintegrant includes, for example, starch, agar, gelatin powder, crystalline cellulose, calcium carbonate, sodium hydrogencarbonate, calcium citrate, dextrin, pectin and calcium carboxymethyl cellulose; the lubricant includes, for example, magnesium stearate, talk, polyethylene glycol, silica and hardened plant oils; the coloring agent includes those substances which are permitted to add to pharmaceutical preparations; and the flavoring agent includes, for example, cocoa powder, menthol, empasm, peppermint oil, borneol and cinammon powder. These tablets or granules may be sugarcoated or coated with other appropriate coating. In the case where a syrup or a preparation for injection is to be prepared, the compound of the present invention or a pharmaceutically acceptable salt thereof may be added with a pH adjusting agent, a resolvent, an isotonizing agent and so on, if necessary, together with a solubilizer, a stabilizing agent and so on, and formulated in a conventional manner. For a pharmaceutical preparation for external application, the process for production of the preparation is not particularly limited and any of the conventional methods may be employed. As the base materials for the preparation, various materials which are conventionally used in drugs, quasi-drugs, cosmetics etc. Specific examples of the base materials to be used include animal and plant oils, mineral oils, ester oils, waxes, higher alcohols, fatty acids, silicone oils, surfactants, phospholipids, alcohols, polyhydric alcohols, water-soluble polymers, clay minerals, purified water etc. If necessary, pH adjusting agents, antioxidant, chelating agents, antiseptical fungicidal agents, coloring agents, flavoring agents and so on may also be added. However, the base materials for external preparations of the present invention are not limited to these materials. If necessary, agents having a differentiation inducing effect, bloodstream promoting agents, germicides, antiphlogistics, cell activators, vitamins, amino acids, moisturizers, keratin solubilizers and so on may also be added. The amounts of the base materials may be those which are employed for formulation of conventional external preparations.

In the administration of a preparation comprising the compound of the present invention or a pharmaceutically acceptable salt thereof as an active ingredient, the dosage form is not particularly limited, and may be for oral or parenteral administration through conventional routes. For example, it can be formulated and administered in the dosage form of tablets, powder, granules, capsules, syrup, troche, inhalant, suppository, injection, ointment, ophthalmic ointment, eye drops, nose drops, ear drops, poultice, lotion etc. The dosage of the pharmaceutical preparation of the present invention may be suitably selected depending on the severity of the symptoms, the age, sex and body weight of a patient, the route of the administration, the type of the salt, specific kinds of the disease etc.

The following Referential Examples, Examples (also a pharmacologically acceptable salt thereof, hydrates thereof and a medicament or medical composition comprising the compound) and Test examples are given merely to illustrate the present invention. It should be understood, however, that these examples are not intended to limit the compound of the present invention in any way. Those skilled in the art, therefore, will appreciate that, in addition to the examples below, various modification of the scope of the appended claims are possible to achieve the best possible practice of the present invention and that such modifications are also included in the scope of the appended claims.

REFERENTIAL EXAMPLE 1

4-[(5,6-Dimethoxy-1-indanon)-2-yl]methyl-1-(1,3-dioxolan-2-yl)methylpiperdine

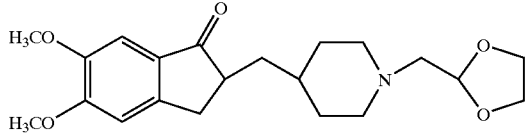

4-[(5,6-Dimethoxy-1-indanon)-2-yl]methylpiperidine (1.00 g, 3.46 mmol) was dissolved in N,N-dimethylformamide (DMF) (10 ml), followed by adding triethylamine (0.96 ml, 6.92 mmol) and 2-bromomethyl-1,3-dioxolane (0.43 ml, 4.13 mmol) thereto. The mixture was stirred overnight at 60° C. and then allowed to cool to room temperature. After adding water (50 ml) thereto, the mixture was extracted with ethyl acetate (50 ml). The organic layer was washed with brine (50 ml×2), dried ($MgSO_4$) and then evaporated. The resulting residue was purified by silica gel column chromatography (NH-silica gel; n-hexane/ethyl acetate system) and then recrystallized from ethyl acetate/n-hexane, to give the title compound (0.48 g, yield: 37%) as white crystals. Melting point: 125–126° C.

$^1$H-NMR (400Mz, $CDCl_3$); δ (ppm) 1.27–1.56(4H, m), 1.64–1.78(2H, m), 1.91(1H, ddd, J=4Hz, J=8Hz, J=13.6Hz), 2.09(1H, ddt, J=2.8Hz, J=5.6Hz, J=11.6Hz), 2.58(2H, d, J=4.4Hz), 2.67–2.75(2H, m), 3.02(1H, bdt, J=3.2Hz, J=7.2Hz), 3.24(1H, dd, J=8Hz, J=17.6Hz), 3.84–4.00(4H, m), 3.91(3H, s) 3.97(3H, s), 5.02(1H, t, J=4.4Hz), 6.86(1H, s), 7.17(1H, s). ESI-MS: m/z=376(M+H$^+$).

REFERENTIAL EXAMPLE 2

1-(3-Cyanobenzyl)-4-[(5,6-dimethoxy-1-indanon)-2-yl]methylpiperidine

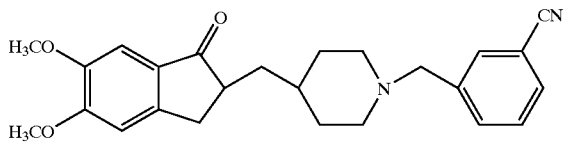

4-[(5,6-Dimethoxy-1-indanon)-2-yl]methylpiperidine (0.60 g, 2.07 mmol) was dissolved in 1,2-dichloroethane (10 ml), followed by adding 3-cyanobenzaldehyde (0.30 ml, 2.29 mmol) thereto. Acetic acid (0.18 ml, 3.16 mmol) and sodium triacetoxyborohydride (0.66 g, 3.11 mmol) were further added thereto, followed by stirring at room temperature for 3 hours. Ethyl acetate (60 ml) was added thereto. The resulting mixture was washed with a saturated aqueous sodium carbonate solution (60 ml) and brine (60 ml), dried ($MgSO_4$), and then evaporated. The resulting residue was purified by silica gel column chromatography (NH-silica gel; n-hexane/ethyl acetate system), to give the title compound as a pale yellow oil (0.84 g, yield: quantitative).

$^1$H-NMR (400Mz, $CDCl_3$)δ: 1.29–1.41(2H, m), 1.47–1.58(1H, m), 1.60–1.78(3H, m), 1.88–2.05(3H, m), 2.67–2.74(2H, m), 2.80–2.89(2H, m), 3.25(1H, dd, J=8Hz, J=17.6Hz), 3.51(2H, s), 3.91(3H, s), 3.96(3H, s), 6.86(1H, s), 7.17(1H, s), 7.39–7.50(1H, m), 7.52–7.70(3H, m). ESI-MS: m/z=405 (M+H$^+$).

REFERENTIAL EXAMPLE 3

4-[(5,6-Dimethoxyl-1-indanon)-2-yl]methyl-1-(2-picolyl)piperidine

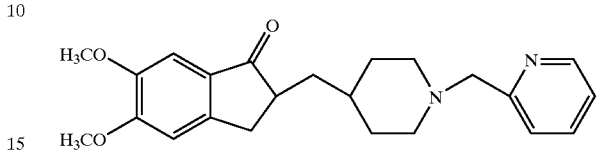

The same procedure as in Referential Example 2 was performed to give the title compound (free form) as a pale yellow oil (yield: 62%).

$^1$H-NMR (400Mz, $CDCl_3$)δ: 1.29–1.58)3H, m), 1.64–1.70(1H, m) 1.72–1.79(1H, m), 1.80–1.96(2H, m), 2.04–2.13(2H, m), 2.67–2.75(2H, m), 2.88–2.96(2H, m), 3.24(1H, dd, J=8Hz, J=17.6Hz), 3.65(2H, s), 3.91(3H, s), 3.96(3H, s), 6.86(1H, s), 7.14–7.17(1H, m), 7.17(1H, s), 7.43(1H, d, J=8Hz), 7.65(1H, dd, J=2Hz, J=7.6Hz), 8.54–8.58(1H, m). ESI-MS: m/z=381 (M+H$^+$).

REFERENTIAL EXAMPLE 4

1[2-(t-Butyldiphenylsilyloxy)methylbenzyl-4-(5,6-dimethoxyl-1-indanon)-2-yl]methylpiperidine

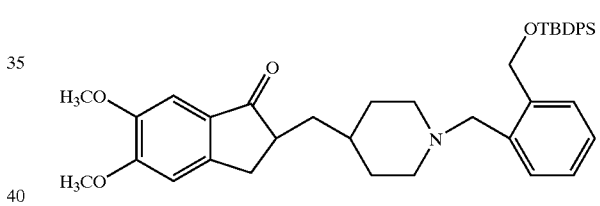

The same procedure as in Referential Example 2 was performed to give the title compound as a pale yellow oil (yield: 94%).

$^1$H-NMR (400Mz, $CDCl_3$)δ: 1.00–1.10(1H, m), 1.11(9H, s), 1.20–1.28(1H, m), 1.32–1.46(1H, m), 1.48–1.55(1H, m), 1.55–1.63(2H, m), 1.79–1.88(3H, m), 2.62–2.71(4H, m), 3.20(1H, dd, J=8Hz, J=17.6H), 3.32(2H, s), 3.91(3H, s), 3.96(3H, s), 4.94(2H, s), 6.85(1H, s), 7.17(1H, s), 7.18–7.46 (9H, m), 7.65–7.73(5H, m).

REFERENTIAL EXAMPLE 5

4-[(5,6-Dimethoxyl-1-indanon)-2-yl]methyl-1-(2-hydroxymethylbenzyl)piperidine

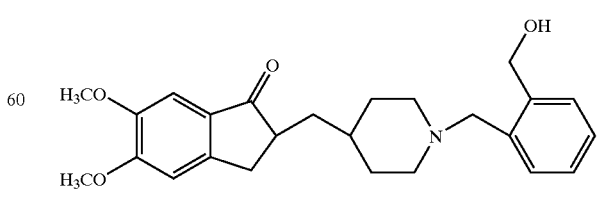

1-[2-(t-Butyldiphenylsilyloxy)methylbenzyl]-4-(5,6-dimethoxy-1-indanon)-2-yl]methylpiperidine (0.10 g, 0.15 mmol) prepared in Referential Example 4 was dissolved in THF (5 ml), and tetra-n-butylammonium fluoride (0.23 ml, 0.23 mmol) was added thereto. After stirring at room temperature for 45 minutes, the mixture was evaporated. The resulting residue was purified by preparative thin layer chromatography (methylene chloride/methanol system), to give the title compound as a pale yellow oil (22 mg, yield: 35%)

$^1$H-NMR (400Mz, CDCl$_3$)δ: 1.20–1.35(4H, m), 1.55–1.68(1H, m) 1.70–1.79(2H, m), 1.86–1.95(1H, m), 2.03–2.13(2H, m), 2.63–2.72(2H, m), 2.91–3.00(2H, m), 3.23(1H, dd, J=8Hz, J=17.6Hz), 3.59(2H, s), 3.90(3H, s), 3.96(3H, s), 4.60(2H, s), 6.84(1H, s), 7.16(1H, s), 7.19–7.37 (4H, m) ESI-MS: m/z=410 (M+H$^+$).

REFERENTIAL EXAMPLE 6

1-[2-(t-Butyldiphenysilyoxy)methylbenzyl]-4-(5,6-dimethoxy-2-flouro-1-indanon)-2-yl]methylpiperidine

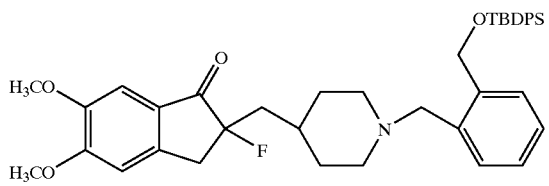

The same procedure as in Referential Example 2 was performed using 4-[(5,6-dimethoxy-1-indanon)-2-yl]methyl-1-(2-hydroxymethylbenzyl)piperidine to give the title compound as a pale yellow oil (yield: 58%).

$^1$H-NMR (400Mz, CDCl$_3$)δ: 0.95–1.20(2H, m), 1.47–1.65(4H, m), 1.75–1.86(2H, m), 1.90–2.01(1H, m), 2.55–2.65(2H, m), 3.19–3.34(1H, m), 3.24(1H, d, J=4.8Hz), 3.29(2H, s), 3.91(3H, s), 3.97(3H, s), 4.92(2H, s), 6.82(1H, s), 7.13–7.47(9H, m), 7.20(1H, s), 7.63–7.72(5H, m).

REFERENTIAL EXAMPLE 7

1-Benzyl-4-[[[5,6-di-(1-propyloxy)]-1-indanon)-2-yl]methylpiperidine

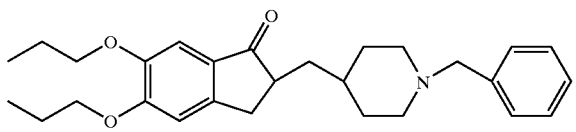

Methyl 3-(3,4-dihydroxyphenyl)propionate (19.8 g, 0.10 mol) was dissolved in DMF (200 ml), and potassium carbonate (33.4 g, 0.24 mol) and 1-propyl iodide (23.6 ml, 0.24 mol) were added thereto. After stirring at 150° C. for 5 hours, the mixture was allowed to cool to room temperature. Ethyl acetate (800 ml) was added thereto, followed by washing with brine (800 ml×3). After drying (MgSO$_4$), the mixture was evaporated. The resulting residue was purified by silica gel column chromatography (n-hexane/ethyl acetate system), to give the title compound as a pale yellow oil (15.6 g, yield; 58%).

The oil (15.6 g, 58.1 mol) was dissolved in THF (100 mg). 1N aqueous sodium hydroxide solution (70 ml) was added thereto, followed by heating under reflux for 1 hour. After allowing to cool to room temperature, the mixture was evaporated. Water (500 ml) was added to the residue and the resulting solution was washed with diethyl ether (400 ml). After acidifying the aqueous layer with 1N hydrochloric acid, it was extracted with ethyl acetate (500 ml) and washed with brine (500 ml). After drying (MgSo$_4$), it was evaporated. The resulting residue was recrystallized from ethyl acetate/n-hexane, to give white crystals (13.2 g, yield: 89%).

The crystals (13.2 g, 51.9 mol) were dissolved in benzene (200 ml), added with thionyl chloride (15.1 ml, 0.207 mol) and then refluxed with heating for 3 hours. After allowing to cool to room temperature, the mixture was evaporated. The resulting residue was dissolved in 1,2-dichloroethane (500 ml) and then added with aluminum chloride (8.30 g, 62.2 mmol). After stirring at 0° C. for 1 hour, ice water (500 ml) was added thereto, and the insoluble matters were filtered off thorough Celite. The organic layer was washed with a saturated aqueous sodium hydrogencarbonate solution (500 ml) and brine (500 ml). After drying (MgSO$_4$), it was evaporated. The resulting residue was recrystallized from methanol, to give white crystals (5.70 g, yield: 44%).

The crystals (5.00 g, 20.1 mmol) were dissolved in THF (50 ml), and a solution (20 ml) of 1-benzyl-4-formylpiperidine (5.73 g, 28.2 mmol) in THF and a solution (10 ml) of 28% sodium methoxide (4.27 g, 22.2 mmol) in THF were added thereto. After stirring at room temperature for 3 hours, ethyl acetate was added thereto, and the resulting solution was washed with brine (300 ml×2). After drying (MgSO$_4$), the mixture was evaporated. The resulting residue was recrystallized from ethyl acetate/n-hexane, to give pale yellowish white crystals (5.53 g, yield: 63%).

FAB-MS: m/z=434 (M+H$^+$).

The above-mentioned crystals (3.00 g, 6.92 mmol) were dissolved in THF (70 ml). To the mixture was added 10% palladium-carbon (0.3 g), followed by hydrogenating at room temperature under atmospheric pressure for 1.5 hours. After removing the catalyst by filtration, the filtrate was evaporated, and the resulting residue was purified by silica gel column chromatography (methylene chloride/methanol system), to give the title compound as a pale yellow oil (2.20 g, yield: 73%).

$^1$H-NMR (400Mz, CDCl$_3$)δ: 1.04(3H, t, J=7.2Hz) 1.07 (3H, t, J=7.2Hz), 1.24–1.45(3H, m), 1.45–1.57(1H, m), 1.64–1.77(2H, m), 1.80–1.95(5H, m), 1.95–2.07(2H, m), 2.63–2.72(2H, m), 2.88–2.97(2H, m), 3.20(1H, dd, J=8Hz, J=17.2Hz), 3.54(2H, s), 3.97(2H, t, J=6.8Hz), 4.03(2H, t, J=6.8Hz), 6.82(1H, s), 7.15(1H, s), 7.15–7.38(5H, m). FAB-MS: m/z=436 (M+H$^+$).

EXAMPLE 1

1-Benezyl-4-[(5,6-diethoxy-2-flouro-1-indanon)-2-yl]methylpiperidine Hydrochloride

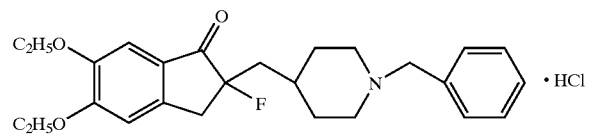

The following reactions were conducted in nitrogen atmosphere.

1-Benzyl-4-((5,6-diethoxy-1-indanon)-2-yl]methylpiperidine (0.20 g, 0.49 mmol) was dissolved in tetrahydrofran (THF) (10 ml). After cooling to −78° C., a 1.0 M solution of lithium bis(trimethylsilyl)amide in THF (0.59 ml., 0.59 mmol) was poured thereinto. After elevating the temperature of the solution from −78° C. to −20° C. over 45 minutes, it was cooled again to −78° C., and a solution (2 ml) of N-fluorobenzenesulfonimide (0.23 g, 0.73 mmol) in THF was poured thereinto. After gradually elevating the temperature of the solution from −78° C. to room temperature and stirring for 4 hours, a saturated aqueous ammonium chloride solution (30 ml) was added to the solution, and the solution was extracted with ethyl acetate (30 ml). The organic layer was washed with brine, dried (MgSO$_4$), and then evaporated. The resulting residue was purified by silica gel column chromatography (NH-silica gel; methylene chloride/methanol system), to give the title compound in a free form as a pale yellow oil (0.12 g, yield: 57%).

The oil was converted into a hydrochloride by a conventional method and then recrystallized from ethanol/isopropyl ether, to give the title compound as pale yellow crystals.
Hydrochloride: Melting point: 195–198° C.
$^1$H-NMR (400Mz, CDCl$_3$); δ (ppm) 1.47 (3H, t, J=7.2Hz), 1.52(3H, t, J=7.2Hz), 1.70–1.78(1H, m), 1.86–1.96(2H, m), 2.00–2.23(4H, m), 2.56–2.74(2H, m), 3.16(1H, dd, J=9.2Hz, J=17.2Hz), 3.28(1H, dd, J=17.2Hz, J=21.6Hz), 3.43(2H, dd, J=12Hz, J=20Hz), 4.10(2H,q, J=7.2Hz), 4.12(2H, s), 4.18(2H,q, J=7.2Hz), 6.77(1H, s), 7.12(1H, s), 7.40–7.50(3H, m), 7.55–7.65(2H, m), 12.32 (1H, bs). ESI-MS: m/z=426 (M+H$^+$).

EXAMPLE 2

1-Benzyl-4-[(5,6-dimethyl-2-flouro-1-indanon)-2-yl]piperidine

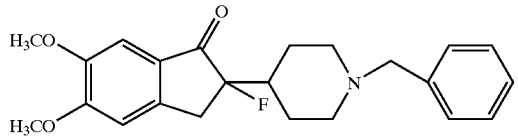

The same procedure as in Example 1 was performed, to give the title compound as a pale yellow oil (yield: 84%).
$^1$H-NMR (500Mz, CDCl$_3$); δ (ppm) 1.14–1.30(2H, m), 1.50–1.63(1H, m), 1.89–2.07(3H, m), 2.10–2.20(1H, m), 2.83(1H, bd, J=11Hz), 3.00(1H, bd, J=11Hz), 3.10(1H, dd, J=17.5Hz, J=23.5Hz), 3.40(1H, dd, J=11Hz, J=17.5Hz), 3.49(2H, s), 3.90(3H, s), 3.98(3H, s), 6.83(1H, s), 7.17(1H, s), 7.20–7.32(5H, m) ESI-MS: m/z=384 (M+H$^+$).

EXAMPLE 3

1-Benzyl-4-[[2-[5,6-dimethoxy-2-flouro-1-indanon)-2-yl]ethyl]piperidine

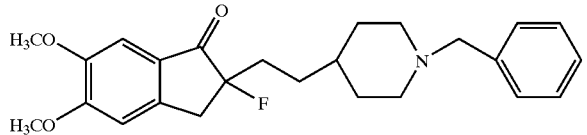

The same procedure as in Example 1 was performed, to give the title compound as a pale yellow oil (yield: 61%).
$^1$H-NMR (270Mz, CDCl$_3$); δ (ppm) 1.14–1.48(5H, m), 1.55–2.12(6H, m), 2.82–2.94(2H, m), 3.21(2H, bs), 3.49 (2H, s), 3.91(3H, s), 3.98(3H, s), 6.84(1H, s), 7.20(1H, s), 7.22–7.34(5H, m). ESI-MS: m/z=412 (M+H$^+$).

EXAMPLE 4

4-[(5,6-Dimethoxy-2-flouro-indanon)-2-yl]methyl-1-(3-flourobenzyl)piperidine Hydrochloride

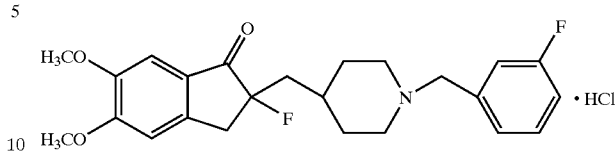

The same procedure as in Example 1 was performed, to give the title compound (free form) as a pale yellow oil (yield: 62%).

The compound was converted into a hydrochloride by a conventional method, and the hydrochloride was recrystallized from ethanol, whereby the title compound was obtained as pale yellow crystals.
Hydrochloride: Melting point: 213–215° C.
$^1$H-NMR (400Mz, CDCl$_3$); ° (ppm) 1.76–1.82(1H, m), 1.88–1.97(2H, m), 2.06–2.24(4H, m), 2.62–2.78(2H, m), 3.19(1H, dd, J=9.2Hz, J=17.2Hz), 3.31(1H, dd, J=17.2Hz, J=21.6Hz), 3.45(2H, dd, J=12.8Hz, J=18.8Hz), 3.91(3H, s), 3.98(3H, s), 4.14(2H, d, J=4Hz), 6.75(1H, s), 7.12–7.20(1H, m), 7.14(1H, s), 7.36–7.54(3H, m), 12.43(1H, bs). ESI-MS: m/z=416 (M+H$^+$).

EXAMPLE 5

4-[(5,6-Dimethoxy-2-flouro-1-indanon)-2-yl]methyl-1-(3-methylbenzyl)piperidine Hydrochoride

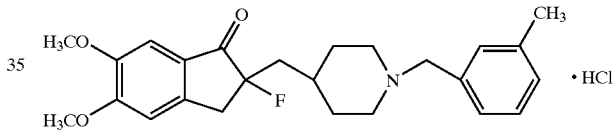

The same procedure as in Example 1 was performed, to give the title compound (free form) as a pale yellow oil (yield: 67%).

The compound was converted into a hydrochloride by a conventional method, and the hydrochloride was recrystallized from ethanol/isopropyl ether, whereby the title compound was obtained as pale yellow crystals.
Hydrochloride: Melting point: 219–221° C. (decomposed).
$^1$H-NMR (400Mz, CDCl$_3$); δ (ppm) 1.72–1.80(1H, m), 1.86–1.98(2H, m), 2.00–2.24(4H, m), 2.40(3H, s), 2.54–2.74(2H, m), 3.14–3.50(4H, m), 3.91(3H, s), 3.98(3H, s), 4.09(2H, bs), 6.81(1H, s), 7.14(1H, s), 7.23–7.40(4H, m), 12.28(1H, bs). ESI-MS: m/z=412 (M+H$^+$).

EXAMPLE 6

1-(-Cyclohexylmethyl-4-[(5,6-dimethoxy-2-flouro-1-indanon)-2-yl]methylpiperidine Hydrochloride

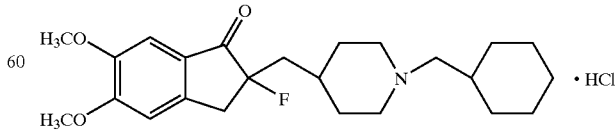

The same procedure as in Example 1 was performed to obtained the title compound (a free form) as a pale yellow oil (yield: 57%).

The compound was converted into a hydrochloride by a conventional method, and the hydrochloride was recrystallized from ethanol, whereby the title compound was obtained as pale yellow crystals.

Hydrochloride: Melting point: 215–225° C. (decomposed).

$^1$H-NMR (400Mz, CDCl$_3$); ° (ppm) 0.99–1.10(2H, m), 1.20–1.28(1H, m), 1.28–1.42(2H, m), 1.60–1.90(9H, m), 1.92–2.22(4H, m), 2.90–3.00(4H, m), 3.28(1H, dd, J=17.2Hz, J=22.4Hz), 3.41(1H, dd, J=11.6Hz, J=17.2Hz), 3.54(2H, bd, J=12Hz), 3.86(3H, s), 3.95(3H, s), 7.07(1H, s), 7.18(1H, s). ESI-MS: m/z=404 (M+H$^+$).

EXAMPLE 7

4-[(5,6-Dimethoxy-2-flouro-1-indanon-2-yl]methyl-1-(1,3-dioxolan-2-yl)methylpiperidine Hydrochloride

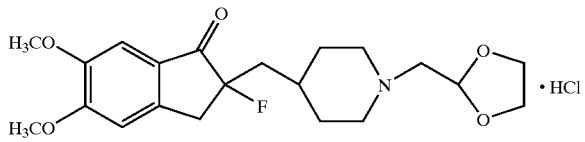

The same procedure as in Example 1 was performed using 4-[(5,6-dimethoxy-1-indanon)-2-yl]methyl-1-(1,3-dioxolan-2-yl)methylpiperidine prepared in Referential Example 1, to give the title compound (free form) as a pale yellow oil (yield: 6.5%).

The compound was converted into a hydrochloride by a conventional method, and the hydrochloride was recrystallized from ethanol/isopropyl ether, to give the title compound as pale yellow crystals.

Hydrochloride: Melting point: 143–145° C.

$^1$H-NMR (400Mz, CDCl$_3$); ° (ppm) 1.75–2.25(7H, m), 2.76–2.92(2H, m), 3.11(2H, bs), 3.18–3.40(2H, m), 3.68 (2H, t, J=12Hz), 3.58–4.05(4H, m), 3.92(3H, s), 3.99(3H, s), 5.59(1H, t, J=4Hz), 6.83(1H, s), 7.17(1H, s), 12.54(1H, bs). ESI-MS: m/z=394 (M+H$^+$).

EXAMPLE 8

1-(4-Benzyloxybenzyl)-4-[(5,6-dimethoxy-2-flouro-1-indanon)-2-yl]methylpiperidine

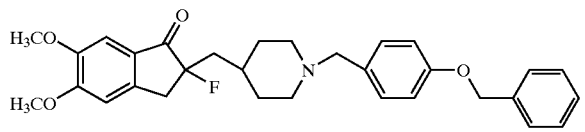

The same procedure as in Example 1 was performed, to give the title compound as a pale yellow oil (yield: 58%).

$^1$H-NMR (270Mz, CDCl$_3$); δ (ppm) 1.32–1.52(2H, m), 1.56–1.80(4H, m), 1.90–2.10(3H, m), 2.86(2H, bd, J=11.7Hz), 3.25(1H, d, J=3.2Hz), 3.31(1H, s), 3.45(2H, s), 3.91(3H, s), 3.98(3H, s), 5.05(2H, s), 6.83(1H, s), 6.91(1H, s), 6.94(1H, s), 7.18–7.46 (8H, m) ESI-MS: m/z=504 (M+H$^+$).

EXAMPLE 9

1-(3-Cyanobenzyl-4-[(5,6-dimethoxy-2-flouro-1-indanon)-2-yl]methylpiperidine Hydrochloride

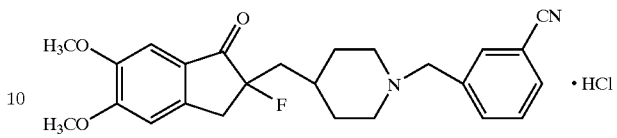

The same procedure as in Example 1 was performed using 1-(3-cyanobenzyl)-4-[(5,6-dimethoxy-1-indanon)-2-yl]methylpiperidine prepared in Referential Example 2, to give the title compound (free form) as a pale yellow oil (yield: 16%).

The compound was converted into a hydrochloride by a conventional method, and the hydrochloride was recrystallized from ethanol/t-butyl methyl ether, to give the title compound as pale yellowish white crystals.

Melting point: 139–141° C.

$^1$H-NMR (400Mz, CDCl$_3$)δ: 1.60–2.28(7H, m), 2.65–2.83(2H, m), 3.14–3.52(4H, m), 3.91(3H, s), 3.98(3H, s), 4.19(2H, bs), 6.82(1H, s), 7.15(1H, s), 7.62(1H, t, J=7.6Hz), 7.75(1H, t, J=7.6Hz), 7.85(1H, s), 8.28(1H, d, J=8Hz), 12.62(1H, bs) ESI-MS: m/z=423 (M+H$^+$).

EXAMPLE 10

4-[(5,6-Dimethoxy-2-flouro-1-indanon)-2-yl]methyl-1-(2-picolyl)piperidine Dihydrochloride

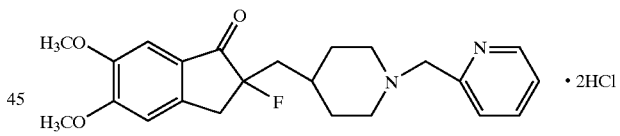

The same procedure as in Example 1 was performed using 4-[(5,6-dimethoxy-1-indanon)-2-yl]methyl-1-(2-picolyl)piperidine prepared in Referential Example 3, to give the title compound (free form) as a pale yellow oil (yield: 34%).

The compound was converted into a hydrochloride by a conventional method, and the hydrochloride was recrystallized from ethanol/t-butyl methyl ether, to give the title compound as pale yellowish white crystals.

Melting point: 177–180° C.

$^1$H-NMR (400Mz, CDCl$_3$)δ: 1.75–2.20(6H, m), 3.17–3.42(7H, m), 3.92(3H, s), 3.99(3H, s), 4.90(2H, bs), 6.83(1H, s), 7.18(1H, s), 7.91(1H, bs), 8.45(1H, bs), 8.70–8.78(1H, m), 9.12(1H, bs). (no proton of hydrochloric acid was observed). ESI-MS: m/z=399 (M+H$^+$).

EXAMPLE 11

4-[(5,6-Dimethoxy-2-flouro-1-indanon)-2-yl]methyl-1-(3-nitrobenzyl)piperidine Hydrochloride

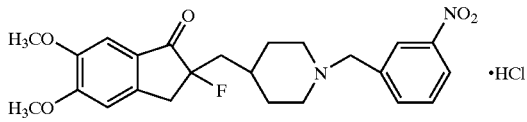

The same procedure as in Example 1 was performed, to give the title compound (free form) as a pale yellow oil (yield: 80%).

The compound was converted into a hydrochloride by a conventional method, and the hydrochloride was recrystallized from ethanol, to give the title compound as pale yellowish white crystals.

Melting point: 161–162° C.

$^1$H-NMR (400Mz, CDCl$_3$)δ: 1.74–2.02(4H, m), 2.05–2.26 (3H, m), 2.76–2.94(2H, m), 3.16–3.38(2H, m), 3.43–3.56 (2H, m), 3.91(3H, s), 3.98(3H, s), 4.33(2H, bs), 6.82(1H, s), 7.14(1H, s), 7.70(1H, t, J=8Hz), 8.30(1H, t, J=7.6Hz), 8.40–8.53(2H, m), 12.61(1H, bs) ESI-MS: m/z=443 (M+H$^+$).

EXAMPLE 12

1-Benzyl-4-[(5-methoxy-2-flouro-1-indanon)-2-yl]methylpiperidine Hydrochloride

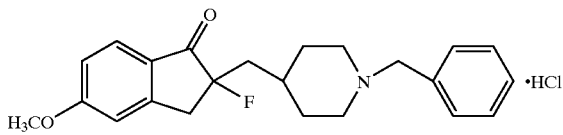

The same procedure as in Example 1 was performed, to give the title compound (free form) as a pale yellow oil (yield: 33%).

The compound was converted into a hydrochloride by a conventional method, and the hydrochloride was recrystallized from ethanol/t-butyl methyl ether, to give the title compound as pale yellowish white crystals.

Melting point: 194–195° C.

$^1$H-NMR (400Mz, CDCl$_3$)δ: 1.63–2.23(7H, m), 2.56–2.74(2H, m), 3.21(1H, dd, J=9.2Hz, J=17.2Hz), 3.34 (1H, dd, J=17.2Hz, J=21.6Hz), 3.37–3.48(2H, m), 3.90(3H, s,), 4.12(2H, bs), 6.83(1H, s), 6.94(1H, dd, J=2Hz, J=8.4Hz), 7.42–7.47(3H, m), 7.57–7.64(2H, m) 7.69(1H, d, J=8.4Hz), 12.34(1H, bs). ESI-MS: m/z=368 (M+H$^+$).

EXAMPLE 13

1-Benzyl-4-[(2-flouro-1-indanon)-2-yl]methylpiperidine Hydrochloride

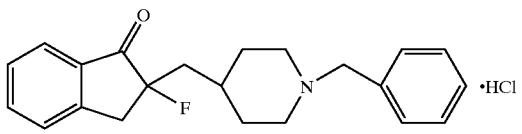

The same procedure as in Example 1 was performed, to give the title compound (free form) as a pale yellow oil (yield: 57%).

The compound was converted into a hydrochloride by a conventional method, and the hydrochloride was recrystallized from ethanol/t-butyl methyl ether, to give the title compound as pale yellowish white crystals.

Melting point: 187–189° C.

$^1$H-NMR (400Mz, CDCl$_3$)δ: 1.72–2.23(7H, m), 2.57–2.74(2H, m) 3.27(1H, dd, J=9.2Hz, J=17.2Hz), 3.40 (1H, dd, J=17.2Hz, J=21.6Hz), 3.37–3.49(2H, m), 4.13(2H, d, J=4.4Hz), 7.38–7.50(5H, m), 7.58–7.64(2H, m), 7.67(1H, t, J=7.6Hz), 7.76(1H, d, J=7.2Hz), 12.37(1H, bs). ESI-MS: m/z=338 (M+H$^+$).

EXAMPLE 14

1-Benzyl-4-[3-[5,6-dimethoxy-2-flouro-1-indanon)-2-yl]propyl]piperidine Hydrochloride

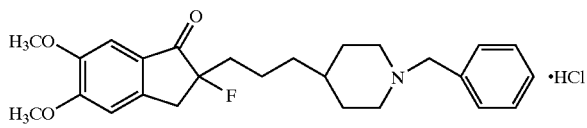

The same procedure as in Example 1 was performed, to give the title compound (free form) as a pale yellow oil (yield: 18%).

The compound was converted into a hydrochloride by a conventional method, and the hydrochloride was recrystallized from ethanol/t-butyl methyl ether, to give the title compound as pale yellowish white crystals.

Melting point: 194–195° C.

$^1$H-NMR (400Mz, CDCl$_3$)δ: 1.30–1.53(5H, m), 1.66–1.88(3H, m), 1.89–2.05(3H, m), 2.55–2.70(2H, m), 3.24(2H, d, J=15.6Hz), 3.40–3.52(2H, m), 3.91(3H, s), 3.99(3H, s), 4.17(2H, bs), 6.86(1H, s), 7.18(1H, s), 7.44(3H, bs), 7.61(2H, bs), 11.90(1H, bs) ESI-MS: m/z=426 (M+H$^+$).

EXAMPLE 15

4-[(5,6-Dimethoxy-2-flouro-1-indanon)-2-yl]methyl-1-(4-hydroxybenzyl)piperidine Hydrochloride

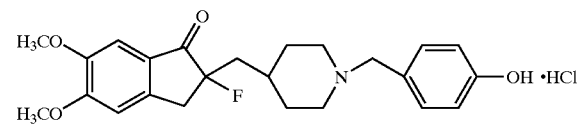

1-(4-Bezyloxybenzyl)-4-[(5,6-dimethoxy-2-fluoro-1-indanon)-2-yl]methylpiperidine (Example 8) (41 mg, 0.081mmol) was dissolved in THF (4 ml), and 10% palladium-carbon (10 mg) was added thereto. The resulting mixture was hydrogenated at room temperature under ambient pressure for 4 hours. The catalyst was removed by filtration, and the filtrate was evaporated. The residue was purified by preparative thin layer chromatography (methylene chloride/methanol), to give the title compound (free form) as a pale yellow oil (13 mg, yield: 39%).

The compound was converted into a hydrochloride by a conventional method, and the hydrochloride was solidified with ethanol/t-butyl methyl ether, to give the desired compound as a pale yellowish white amorphous.

$^1$H-NMR (400Mz, CDCl$_3$)δ: 1.70–2.25(8H$_{1-6}$ m), 2.65–2.88(2H m), 3.18–3.48(4H, m), 3.89(3H, s), 3.97(3H, s), 4.05(2H, bs), 6.85(1H, bs), 6.94(2H, bs), 7.13(1H, s), 7.35(2H, bs), 10.66(1H, bs). ESI-MS: m/z=414 (M+H$^+$).

EXAMPLE 16

4-[(5,6-Dimethoxy-2-flouro-1-indanon)-2-yl]methyl-1-(2-hydroxymethylbenzyl)piperidine Hydrochoride

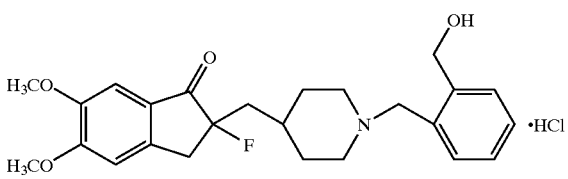

The same procedure as in Referential Example 5 was performed using 1-[2-(t-butyldiphenylsilyloxy)methylbenzyl]-4-[(5,6-dimethoxy-2-fluoro-1-indanon)-2-yl]methylpiperidine prepared in Referential Example 6, to give the title compound (free form) as a pale yellow oil (yield: 64%).

The compound was converted into a hydrochloride by a conventional method and the hydrochloride was freeze-dried, to give the title compound as a pale yellowish white amorphous.

$^1$H-NMR (400Mz, CDCl$_3$)δ: 1.70–2.03(5H, m), 2.05–2.28(3H, m), 2.93–3.15(2H, m), 3.20–3.36(2H, m), 3.55–3.70(2H, m), 3.90(3H, s), 3.98(3H, s), 4.42(2H, bs), 4.86(2H, bs), 6.85(1H, s), 7.13(1H, s), 7.30–7.45(3H, m), 7.45–7.60(1H, m). (no proton of hydrochloric acid was observed.) ESI-MS: m/z=428 (M+H$^+$).

EXAMPLE 17

1-Benzyl-4-[[[5,6-di-(1-propyloxy)]-2-flouro-1-indanon-2-yl]methylpiperidine Hydrochloride

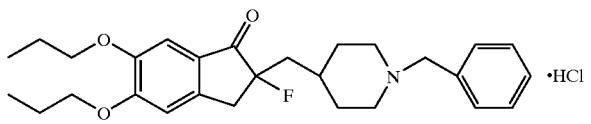

The same procedure as in Example 1 was performed using 1-benzyl-4-[[[5,6-di-(1-propyloxy)]-1-indanon]-2-yl]methylpiperidine prepared in Referential Example 7, to give the title compound (free form) as a pale yellow oil (yield: 33%).

The compound was converted into a hydrochloride by a conventional method, and the hydrochloride was recrystallized from ethanol/t-butyl methyl ether, to give the title compound as pale yellowish white crystals.

Melting point: 211–214° C. (decomposed).

$^1$H-NMR (400Mz, CDCl$_3$)δ: 1.04(3H, t, J=7.2Hz) 1.07(3H, t, J=7.2Hz), 1.70–2.23(13H, m), 3.10–3.35(2H, m), 3.38–3.52(2H, m), 3.96(2H, t, J=6.4Hz), 4.04(2H, t, J=6.4Hz), 4.15(2H, bs), 6.77(1H, s), 7.12(1H, s), 7.45(3H, bs), 7.60(2H, bs), 12.09(1H, bs) ESI-MS: m/z=454 (M+H$^+$).

EXAMPLE 18

4-[(5,6-Dimethoxy-2-flouro-1-indanon)-2-yl]methyl-1-(2-flourobenzyl)piperidine Hydrochloride

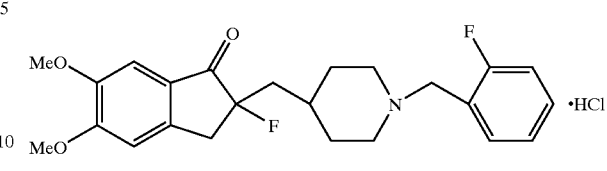

The same procedure as in Example 1 was performed to obtain the title compound (free form) as a pale yellow oil (yield: 57%).

The compound was converted into a hydrochloride by a conventional method, and the hydrochloride was recrystallized from ethanol/t-butyl methyl ether, to give the title compound as pale yellowish white crystals.

Melting point: 203–208° C. (decomposed).

$^1$H-NMR (400Mz, CDCl$_3$)δ: 1.74–2.00(3H, m), 2.00–2.26(4H, m), 2.64–2.82(2H, m), 3.15–3.25(1H, m), 3.29(1H, dd, J=16.8Hz, J=38.4hz), 3.40–3.54(2H, m), 3.90(3H, s), 3.98(3H, s), 4.22(2H, s), 6.82(1H, s), 7.12–7.18(2H, m), 7.26–7.32(1H, m), 7.46(1H, bdd, J=6.4Hz, J=13.6Jz), 7.92(1H, bt, J=6.4hz), 12.42(1H, bs). ESI-MS: m/z=416 (M+H$^+$).

EXAMPLE 19

4-[(5,6-Dimethoxy-2-flouro-1-indanon-2-yl]methyl-1-(4-flourobenzyl)piperidine Hydrochloride

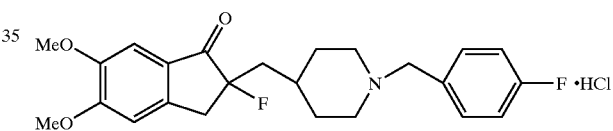

The same procedure as in Example 1 was performed, to give the title compound (free form) as a pale yellow oil (yield: 53%).

The compound was converted into a hydrochloride by a conventional method, and the hydrochloride was recrystallized from ethanol/t-butyl methyl ether, to give the title compound as pale yellowish white crystals.

Melting point: 215–220° C. (decomposed).

$^1$H-NMR (400Mz, CDCl$_3$)δ: 1.70–1.98(3H, m), 2.04–2.26(4H, m), 2.58–2.74(2H, m), 3.14–3.24(1H, m), 3.29(1H, dd, J=17.2Hz, J=38.4Ha), 3.37–3.50(2H, m), 3.91(3H, s), 3.98(3H, s), 4.11(2H, s), 6.82(1H, s), 7.10–7.17(3H, m), 7.64–7.72(2H, m), 12.34(1H, bs) ESI-MS: m/z=416 (M+H$^+$).

Pharmacological Test Example

Hereinbelow, a pharmacological test example is shown to illustrate the usefulness of the compound of the present invention as a medicament. Inhibitory effect on acetylcholinesterase in vitro 1) Test Method Using a rat brain homogenate as a source of acetylcholinesterase, the esterase activity was determined in accordance with the method of Ellman et al[1]. Acethylthiocholine (as a substrate), a test compound and DTNB (5,5'-dithiobis(2-nitrobenzoic acid)) were added to the mouse brain homogenate, and then incubated. Then, the resulting yellow product produced by the reaction of the resulting thiocholine with DTNB was determined for the change in absorbanceat 412 nm, to determine the acethylcholinesterase activity.

[1]; Ellman. G. L., Courtney, K. D., Andres, V. and Featherstone, R. M., (1961), Biochem. Pharmacol., 7, 88–95.

The inhibitory effect of each test compound on acethylcholinesterase was determined in terms of 50% inhibitory concentration ($IC_{50}$).

2) Test Compounds

Each of the compounds was dissolved in physiological saline for use as a test sample.

3) Results

TABLE 1

| Ex. No. | $IC_{50}$ (nM) |
| --- | --- |
| 1 | 0.38 |
| 4 | 0.47 |
| 5 | 0.82 |
| 6 | 1.7 |
| 11 | 0.7 |
| 12 | 1.2 |
| 14 | 1.4 |
| 15 | 0.32 |
| 17 | 0.89 |
| Donepezilhydrochloride | 6.7 |

The above results clearly show the superior effect of the compounds of the present invention.

What is claimed is:

1. A compound represented by the following formula (I), or a pharmaceutically acceptable salt thereof or hydrate thereof, provided that 1-benzyl-4-[(5,6-dimethoxy-2-fluoro-1-indanon)-2-yl]methylpiperidine, pharmaceutically acceptable salts thereof and hydrates thereof are excluded,

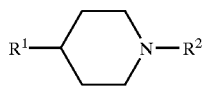

(I)

in the formula, $R^1$ represents any one selected from the group consisting of the following substituents:

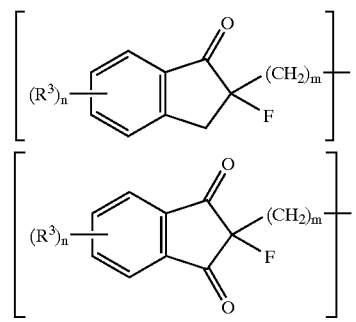

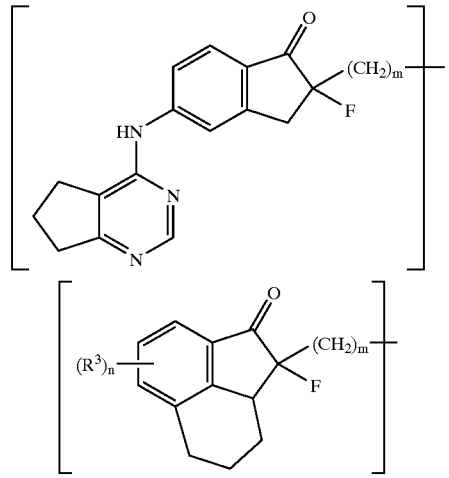

wherein each $R^3$ are the same as or different from each other and each represents hydrogen atom, a halogen atom, hydroxyl group, a $C_{1-6}$ alkyl group, a $C_{3-8}$ cycloalkyl group, a $C_{1-6}$ alkoxy group, a $C_{1-6}$ alkoxyalkoxy group, a halogeno $C_{1-6}$ alkyl group, a hydroxy $C_{1-6}$ alkyl group, a cyano $C_{1-6}$ alkyl group, a halogeno $C_{1-6}$ alkoxy group, a hydroxy $C_{1-6}$ alkoxy group, a cyano $C_{1-6}$ alkoxy group, a lower acyl group, a nitro group, an optionally substituted amino group, an optionally substituted amide group, mercapto group or a $C_{1-6}$ thioalkoxy group; $R^4$ represents hydrogen atom or a $C_{1-6}$ alkyl group; the bond represented by the following formula:

=== is a single or double bond; m is 0 or an integer of 1 to 6; n is an integer of 1 to 4; and p is an integer of 1 or 2; and $R^2$ represents a $C_{3-8}$ cycloalkylmethyl group, 2,2-(alkylenedioxy)ethyl group or a group represented by the formula:

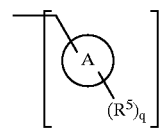

wherein the ring A is benzene ring or a heterocyclic ring; each $R^5$ are the same as or different from each other and each represents hydrogen atom, a halogen atom, hydroxyl group, nitrile group, a $C_{1-6}$ alkyl group, a $C_{3-8}$ cycloalkyl group, a $C_{1-6}$ alkoxy group, a $C_{1-6}$ alkoxyalkoxy group, an aryloxy group, an aralkyloxy group, a halogeno $C_{1-6}$ alkyl group, a hydroxy $C_{1-6}$ alkyl group, a cyano $C_{1-6}$ alkyl group, a halogeno $C_{1-6}$ alkoxy group, a hydroxy $C_{1-6}$ alkoxy group, a cyano $C_{1-6}$ alkoxy group, a lower acyl group, a nitro group, an optionally substituted amino group, an optionally substituted amide group, mercapto group or a $C_{1-6}$ thioalkoxy group, and two of the $R^5$ groups may together form an aliphatic ring, an aromatic ring, a heterocyclic ring or an alkylenedioxy ring; and q is 0 or an integer from 1 to 5.

2. The compound according to claim 1, or a pharmaceutically acceptable salt thereof or hydrate thereof, wherein $R^1$ is a group represented by the formula:

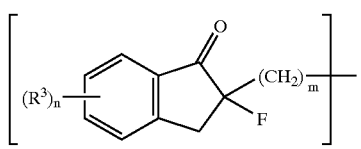

wherein R³, m and n have the same meanings as defined above.

3. The compound according to claim 1, or a pharmaceutically acceptable salt thereof or hydrate thereof, wherein R² is a group represented by the formula:

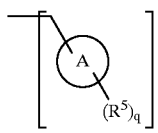

wherein the ring A, R⁵ and q have the same meanings as defined above.

4. The compound according to claim 3, or a pharmaceutically acceptable salt thereof or hydrate thereof, wherein the ring A is a group represented by the formula:

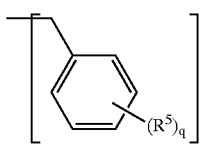

wherein R⁵ and q have the same meanings as defined above.

5. The compound according to claim 3, or a pharmaceutically acceptable salt thereof or hydrate thereof, wherein the ring A is an aromatic heterocyclic ring.

6. The compound according to claim 3, or a pharmaceutically acceptable salt thereof or hydrate thereof, wherein the ring A is pyridine ring.

7. The compound according to any of claims 1 to 6, or a pharmaceutically acceptable salt thereof or hydrate thereof, wherein q is an integer of 1 or 2.

8. The compound according to claim 1, or a pharmaceutically acceptable salt thereof or hydrate thereof, wherein the compound is selected from the group consisting of:

(1) 1-benzyl-4-[(5,6-diethoxy-2-fluoro-1-indanon)-2-yl]methylpiperidine;

(2) 1-benzyl-4-[(5,6-dimethoxy-2-fluoro-1-indanon)-2-yl]piperidine;

(3) 1-benzyl-4-[2-[(5,6-dimethoxy-2-fluoro-1-indanon)-2-yl]ethyl]piperidine;

(4) 4-[(5,6-dimethoxy-2-fluoro-1-indanon)-2-yl]methyl-1-(3-fluorobenzyl)piperidine;

(5) 4-[(5,6-dimethoxy-2-fluoro-1-indanon)-2-yl]methyl-1-(3-methylbenzyl)piperidine;

(6) 1-cyclohexylmethyl-4-[(5,6-dimethoxy-2-fluoro-1-indanon)-2-yl]methylpiperidine;

(7) 4-[(5,6-dimethoxy-2-fluoro-1-indanon)-2-yl]methyl-1-(1,3-dioxolan-2-yl)methylpiperidine; and (8) 1-(4-benzyloxybenzyl)-4-[(5,6-dimethoxy-2-fluoro-1-indanon)-2-yl]methylpiperidine.

9. A pharmaceutical composition comprising, as an active ingredient, the compound according to claim 1, or a pharmaceutically acceptable salt thereof or hydrate thereof; and a pharmaceutically acceptable carrier.

10. The pharmaceutical composition according to claim 9, which is an acetylcholinesterase inhibitor.

11. The pharmaceutical composition according to claim 9, which is an agent for treating or improving various types of senile dementia, cerebrovascular dementia or attention deficit hyperactivity disorder.

12. The pharmaceutical composition according to claim 11, wherein the various types of senile dementia is Alzheimer-type senile dementia.

13. A process for producing the compound as claimed in claim 1, or a pharmaceutically acceptable salt thereof or hydrate thereof, which comprises fluorinating a 4-substituted piperidine compound represented by the following formula (II); and, if required, converting the fluoride into a salt,

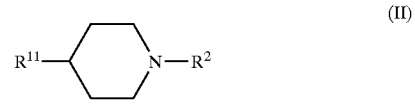

(II)

in the formula, R¹¹ represents any one selected from the group consisting of the following substituents:

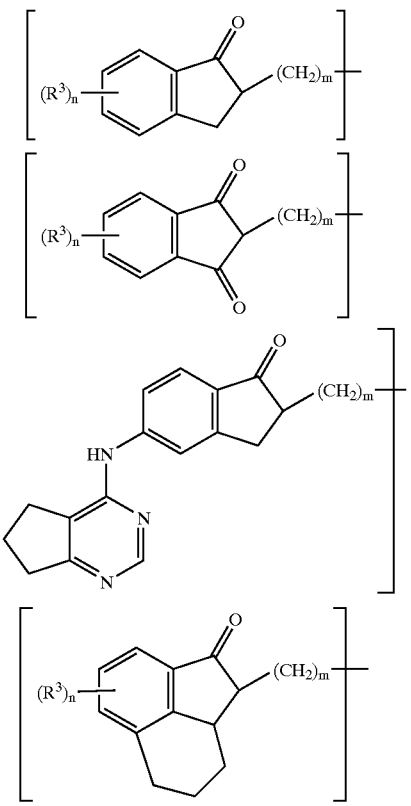

wherein each R³ are the same as or different from each other and each represents hydrogen atom, a halogen atom, hydroxyl group, a $C_{1-6}$ alkyl group, a $C_{3-8}$ cycloalkyl group, a $C_{1-6}$ alkoxy group, a $C_{1-6}$ alkoxyalkoxy group, a halogeno $C_{1-6}$ alkyl group, a hydroxy $C_{1-6}$ alkyl group, a cyano $C_{1-6}$ alkyl group, a halogeno $C_{1-6}$ alkoxy group, a hydroxy $C_{1-6}$ alkoxy group, a cyano $C_{1-6}$ alkoxy group, a lower acyl group, a nitro group, an optionally substituted amino group, an optionally substituted amide group, mercapto group or a $C_{1-6}$ thioalkoxy group; R⁴ represents hydrogen atom or a $C_{1-6}$ alkyl group; the bond represented by the following formula:

=== is a single or double bond; m is 0 or an integer of 1 to 6; n is an integer of 1 to 4; and p is an integer of 1 or 2; and $R^2$ represents a $C_{3-8}$ cycloalkylmethyl group, 2,2-(alkylenedioxy)ethyl group or a group represented by the formula:

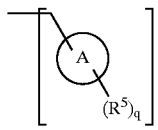

wherein the ring A is benzene ring or a heterocyclic ring; each $R^5$ are the same as or different from each other and each represents hydrogen atom, a halogen atom, hydroxyl group, nitrile group, a $C_{1-6}$ alkyl group, a $C_{3-8}$ cycloalkyl group, a $C_{1-6}$ alkoxy group, a $C_{1-6}$ alkoxyalkoxy group, an aryloxy group, an aralkyloxy group, a halogeno $C_{1-6}$ alkyl group, a hydroxy $C_{1-6}$ alkyl group, a cyano $C_{1-6}$ alkyl group, a halogeno $C_{1-6}$ alkoxy group, a hydroxy $C_{1-6}$ alkoxy group, a cyano $C_{1-6}$ alkoxy group, a lower acyl group, a nitro group, an optionally substituted amino group, an optionally substituted amide group, mercapto group or a $C_{1-6}$ thioalkoxy group, and two of the $R^5$ groups may together form an aliphatic ring, an aromatic ring, a heterocyclic ring or an alkylenedioxy ring; and q is 0 or an integer from 1 to 5, provided that 1-benzyl-4-[(5,6-dimethoxy-1-indanon)-2-yl]methylpiperidine is excluded.

14. The process for producing a compound, or a pharmaceutically acceptable salt thereof or hydrate thereof according to claim 13, wherein the fluorinating agent is N-fluorobenzenesufonimide, 3-cyclohexyl-2-fluoro-2,3-dihydro-3-methyl-1,1-dioxide-1,2-benzisothiazole or 2-fluoro-3,3-dimethyl-2,3-dihydro-1,2-benzisothiazole-1,1-oxide.

15. A pharmaceutical composition comprising a pharmaceutically effective amount of the compound as claimed in claim 1, or a pharmaceutically acceptable salt thereof or hydrate thereof and a pharmaceutically acceptable carrier.

16. A method for treating or ameliorating a disease against which the inhibition of acetylcholinesterase is effective, comprising administering a pharmaceutically effective amount of the compound as claimed in claim 1, or a pharmaceutically acceptable salt thereof or hydrate thereof to a patient.

17. A method for treating or ameliorating various types of senile dementia, cerebrovascular dementia or attention deficit hyperactivity disorder, comprising administering a pharmaceutically effective amount of the compound as claimed claim 1, or a pharmaceutically acceptable salt thereof or hydrate thereof to a patient.

* * * * *